(12) United States Patent
Bacque et al.

(10) Patent No.: US 7,232,834 B2
(45) Date of Patent: Jun. 19, 2007

(54) QUINOLYLPROPYLPIPERIDINE DERIVATIVES, INTERMEDIATES AND COMPOSITIONS CONTAINING THEM, AND PREPARATION THEREFOR

(75) Inventors: Eric Bacque, Gif sur Yvette (FR); Antony Bigot, Massy (FR); Youssef El Ahmad, Creteil (FR); Jean-Luc Malleron, Marcoussis (FR); Serge Mignani, Chatenay Malabry (FR); Baptiste Ronan, Clamart (FR); Michel Tabart, La Norville (FR); Fabrice Viviani, Louvres (FR)

(73) Assignee: Novexel SA, Romainville (FR)

( * ) Notice: Subject to any disclaimer, the term of this patent is extended or adjusted under 35 U.S.C. 154(b) by 618 days.

(21) Appl. No.: 10/659,164

(22) Filed: Sep. 10, 2003

(65) Prior Publication Data

US 2004/0087619 A1 May 6, 2004

(30) Foreign Application Priority Data

Sep. 11, 2002 (FR) .................................. 02 11212

(51) Int. Cl.
*A61K 31/4545* (2006.01)
*C07D 401/06* (2006.01)

(52) U.S. Cl. ...................... 514/315; 514/323; 546/200; 546/236

(58) Field of Classification Search ................ 546/200, 546/236; 514/323, 315
See application file for complete search history.

(56) References Cited

FOREIGN PATENT DOCUMENTS

| GB | 1 253 741 | | 11/1971 |
|---|---|---|---|
| WO | WO 00/43383 | * | 7/2000 |
| WO | WO 01/25227 | | 4/2001 |
| WO | WO 02/40474 | | 5/2002 |

OTHER PUBLICATIONS

Grethe, Guenter et al, "Reinvestigation of the Classical Synthesis of Cinchona Alkaloids. I. A New Synthesis of Homomeroquinene and Quinotoxine," Helvetica Chimica Acta, vol. 56(5), 1973, pp. 1485-1494.*
G. Grethe, et al., "107.Synthesis of 9-epi-Quinine and 9-epi-Quinidine," Helvetica Chimica Acta, 55 Fasc. 3 (1972) No. 107, pp. 1044-1047.
M. Rubtsov, "Synthesis of Racemic N-Acetylhomomeroquinene," Zhurnal Obschei Khimii, vol. 30, No. 5 (J. Gen. Chem, USSR-English translation) (1960), pp. 1514-1522.

* cited by examiner

*Primary Examiner*—Kamal A. Saeed
*Assistant Examiner*—Janet L. Coppins
(74) *Attorney, Agent, or Firm*—Harness, Dickey & Pierce, P.L.C.

(57) ABSTRACT

Quinolylpropylpiperidine derivatives of general formula (I) in which $R_1$ is hydrogen or fluorine, $R_2$ is carboxyl, carboxymethyl or hydroxymethyl, $R_3$ is alkyl substituted either with phenylthio optionally substituted with halogen, hydroxyl, alkyl, alkyloxy, trifluoromethyl, trifluoromethoxy, carboxyl, alkyloxycarbonyl, cyano or amino, or with cycloalkylthio (3 to 7 members) optionally substituted with halogen or trifluoromethyl, or with heteroarylthio (5 to 6 members and 1 to 4 heteroatoms chosen from N, O and S), optionally substituted with halogen, hydroxyl, alkyl, alkyloxy, trifluoromethyl, trifluoromethoxy, carboxyl, alkyloxycarbonyl, cyano or amino or $R_3$ is propargyl substituted by phenyl or heteroaryl as defined above and $R_4$ is alkyl, alkenyl-$CH_2$— or alkynyl-$CH_2$—, cycloalkyl or cycloalkylalkyl, in their various isomeric forms, separate or as mixtures, and also their salts, their preparation process and intermediates and the compositions containing them. These novel derivatives are potent antibacterial agents

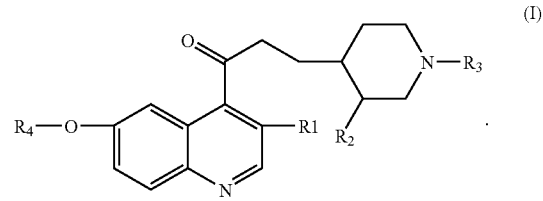

(I)

22 Claims, No Drawings

QUINOLYLPROPYLPIPERIDINE DERIVATIVES, INTERMEDIATES AND COMPOSITIONS CONTAINING THEM, AND PREPARATION THEREFOR

This application claims the benefit of priority of French Patent Application No. 02/11,212, filed Sep. 11, 2002.

The present invention relates to quinolylpropylpiperidine derivatives of general formula (I):

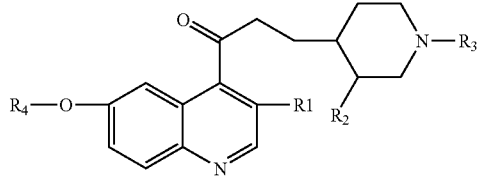

which are active as antimicrobials. The invention also relates to intermediates, compositions containing them, and to their preparation.

In Patent Applications WO 99/37635 and WO 00/43383, there have been described antimicrobial quinolylpropylpiperidine derivatives of general formula:

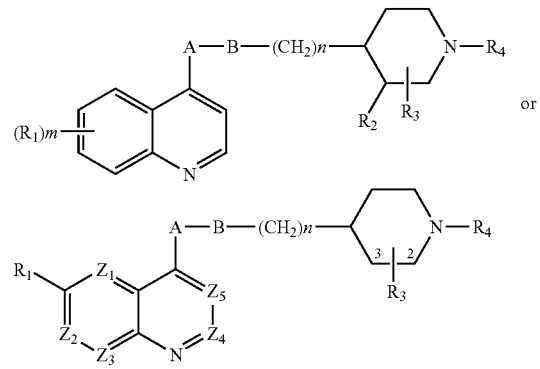

in which the radical $R_1$ is in particular (C1–6)alkoxy, $R_2$ is hydrogen, $R_3$ is at the 2- or 3-position and represents (C1–6)alkyl which may be optionally substituted with 1 to 3 substituents chosen from thiol, halogen, alkylthio, trifluoromethyl, carboxyl, alkyloxycarbonyl, alkylcarbonyl, alkenyloxycarbonyl, alkenylcarbonyl, hydroxyl optionally substituted with alkyl, and the like, $R_4$ is a group —$CH_2$—$R_5$ for which $R_5$ is selected from alkyl, hydroxyalkyl, alkenyl, alkynyl, tetrahydrofuryl, phenylalkyl which is optionally substituted, phenylalkenyl which is optionally substituted, heteroarylalkyl which is optionally substituted, heteroaryl which is optionally substituted, and the like, n is 0 to 2, m is 1 or 2 and A and B are in particular oxygen, sulfur, sulfinyl, sulfonyl, $NR_{11}$, $CR_6R_7$ for which $R_6$ and $R_7$ represent H, thiol, alkylthio, halo, trifluoromethyl, alkenyl, alkenylcarbonyl, hydroxyl, amino, and $Z_1$ to $Z_5$ are N or $CR_{1a}$, and the like.

In European Patent Application EP 30044, there have been described quinoline derivatives which are useful as cardiovascular agents and which correspond to the general formula:

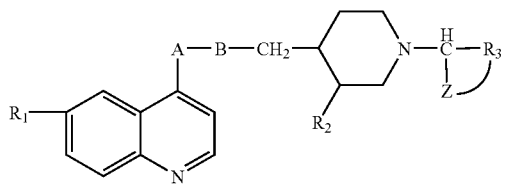

in which $R_1$ is H, OH or in particular alkyloxy, A-B is —$CH_2$—$CH_2$—, —CHOH—$CH_2$—, —$CH_2$—CHOH—, —$CH_2$—CO— or —CO—$CH_2$—, $R_2$ is ethyl or vinyl, $R_3$ is in particular alkyl, hydroxyalkyl, cycloalkyl, hydroxyl, alkenyl, alkynyl, tetrahydrofuryl, phenylalkyl, diphenylalkyl which is optionally substituted, phenylalkenyl which is optionally substituted, benzoyl or benzoylalkyl which is optionally substituted, heteroaryl or heteroarylalkyl which is optionally substituted and Z is H or alkyl or forms with $R_3$ a cycloalkyl radical.

It has now been found, and this is what constitutes the subject of the present invention, that the products of general formula (I) for which:

$R_1$ is a hydrogen or fluorine atom, $R_2$ represents a carboxyl, carboxymethyl or hydroxymethyl radical, $R_3$ represents an alkyl (1 to 6 carbon atoms) radical substituted with a phenylthio radical which may itself carry 1 to 4 substituents chosen from the group consisting of halogen, hydroxyl, alkyl, alkyloxy, trifluoromethyl, trifluoromethoxy, carboxyl, alkyloxycarbonyl, cyano and amino, with a cycloalkylthio radical in which the cyclic portion contains 3 to 7 members, which may itself carry one or more substituents chosen from halogen and trifluoromethyl, or with a 5- to 6-membered heteroarylthio radical comprising 1 to 4 heteroatoms chosen from nitrogen, oxygen and sulfur which may itself carry one or more substituents chosen from the group consisting of halogen, hydroxyl, alkyl, alkyloxy, trifluoromethyl, trifluoromethoxy, carboxyl, alkyloxycarbonyl, cyano and amino or $R_3$ represents a propargyl radical substituted with a phenyl radical which may itself carry 1 to 4 substituents chosen from the group consisting of halogen, hydroxyl, alkyl, alkyloxy, trifluoromethyl, trifluoromethoxy, carboxyl, alkyloxycarbonyl, cyano and amino, or substituted with a 3- to 7-membered cycloalkyl radical which may itself carry one or more substituents chosen from halogen and trifluoromethyl, or substituted with a 5- to 6-membered heteroaryl radical comprising 1 to 4 heteroatoms chosen from nitrogen, oxygen and sulfur and which may itself carry one or more substituents chosen from the group consisting of halogen, hydroxyl, alkyl, alkyloxy, trifluoromethyl, trifluoromethoxy, carboxyl, alkyloxycarbonyl, cyano and amino, and $R_4$ represents an alkyl radical containing 1 to 6 carbon atoms, an alkenyl-$CH_2$— or alkynyl-$CH_2$— radical in which the alkenyl or alkynyl portions contain 2 to 6 carbon atoms, or a cycloalkyl or cycloalkylalkyl radical in which the cycloalkyl portion contains 3 to 8 carbon atoms, in their isomeric, enantiomeric and diastereoisomeric forms, separate or as mixtures, and also their salts, are potent antibacterial agents.

It is understood that the alkyl radicals and portions are in the form of a straight or branched chain and contain (unless otherwise stated) 1 to 4 carbon atoms, and that when $R_3$ carries a halogen substituent, the latter may be chosen from fluorine, chlorine, bromine and iodine, fluorine being preferred.

In the above general formula, when $R_3$ carries a heteroaryl substituent, the latter may be chosen, without limitation, from thienyl, furyl, pyrrolyl, imidazolyl, thiazolyl, oxazolyl, thiadiazolyl, oxadiazolyl, tetrazolyl, pyridyl, pyridazinyl, pyrazinyl and pyrimidinyl.

A subject of the invention is in particular the derivatives of general formula (I) as defined above, in which $R_4$ represents an alkyl radical containing from 1 to 6 carbon atoms, in particular methyl, those in which $R_2$ represents a carboxyl radical and those in which $R_3$ represents an alkyl radical, in particular ethyl, substituted with a phenylthio, cycloalkylthio or heteroarylthio radical optionally substituted as defined above, more particularly those in which $R_3$ represents an ethyl radical substituted with a thienylthio radical or a phenylthio radical substituted with halogen, in particular fluorine, or with trifluoromethyl, cyclohexylthio or cyclopentylthio, and those with the following names:

1-(2-cyclohexylsulfanylethyl)-4-[3-(3-fluoro-6-methoxyquinolin-4-yl)-3-oxo-propyl]piperidine-3-carboxylic acid,
4-[3-(3-fluoro-6-methoxyquinolin-4-yl)-3-oxo-propyl]-1-[3-(2,3,5-trifluorophenyl)prop-2-ynyl]piperidine-3-carboxylic acid,
4-[3-oxo-3-(3-fluoro-6-methoxyquinolin-4-yl)propyl]-1-[2-(2,5-difluorophenylsulfanyl)ethyl]piperidine-3-carboxylic acid,
4-[3-oxo-3-(3-fluoro-6-methoxyquinolin-4-yl)propyl]-1-[2-(2,5-difluorophenylsulfanyl)ethyl]piperidine-3-acetic acid,
4-[3-oxo-3-(6-methoxyquinolin-4-yl)propyl]-1-[2-(2-thienylsulfanyl)ethyl]piperidine-3-carboxylic acid,
4-[3-oxo-3-(6-methoxyquinolin-4-yl)propyl]-1-[3-(2,3,5-trifluorophenyl)prop-2-ynyl]piperidine-3-carboxylic acid,
in their various isomeric forms, separate or as mixtures, as well as their salts.

According to the invention, the products of general formula (I) may be obtained according to process A by condensing the $R_3$ chain with the quinolylpropylpiperidine derivative of general formula (II):

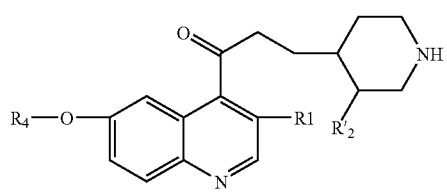

(II)

in which the ketone functional group is, where appropriate, intermediately protected, $R_1$ and $R_4$ are defined as above and $R'_2$ represents a protected carboxyl or carboxymethyl radical, to obtain a quinolylpropylpiperidine derivative of general formula (III):

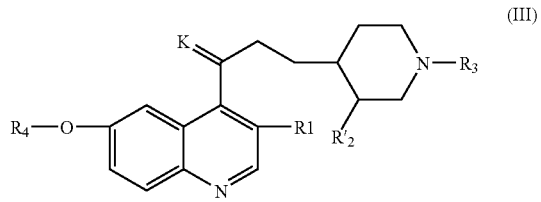

(III)

for which $R_1$, $R'_2$, $R_3$ and $R_4$ are as defined above and K represents an oxygen atom or a ketone-protecting group, then conversion of $R'_2$ to a carboxyl or carboxymethyl radical, and/or, where appropriate, reduction of the carboxyl radical thus obtained or of the protected carboxyl radical which may be represented by $R'_2$ to a hydroxymethyl radical and, optionally, conversion thereof to a carboxymethyl radical according to usual methods, then, where appropriate, separation of the isomers, removal of the acid-protecting radical, removal of the ketone-protecting radical, and/or conversion of the product obtained to a salt.

The condensation of the chain $R_3$ with piperidine is advantageously carried out by the action of a derivative of general formula:

$$R_3\text{—}X \qquad (IV)$$

in which $R_3$ is as defined above and X represents a halogen atom, a methylsulfonyloxy radical, a trifluoromethylsulfonyloxy or p-toluenesulfonyloxy radical, the procedure being carried out in an anhydrous, preferably inert (nitrogen or argon for example) medium, in an organic solvent such as an amide (dimethylformamide for example), a ketone (acetone for example) or a nitrile (acetonitrile for example) in the presence of a base such as a nitrogen-containing organic base (for example triethylamine) or an inorganic base (alkali metal carbonate:potassium carbonate for example) at a temperature of between 20° C. and the reflux temperature of the solvent.

Preferably, a derivative for which X is a bromine or iodine atom is caused to react.

Derivatives of formula (IV) are described or can be prepared as described, for example, in applications WO 200125227 and WO 200240474.

When $R_3$ represents propargyl substituted with phenyl, cycloalkyl or heteroaryl, it may also be preferable to condense a propargyl halide, and then to substitute the chain with a phenyl, cycloalkyl or heteroaryl radical. In this alternative case, the condensation of the propargyl chain is carried out by means of propargyl bromide, under the conditions set out above in the presence, where appropriate, of an alkali metal iodide such as for example potassium or sodium iodide.

When substitution with a phenyl or heteroaryl radical is involved, the reaction is carried out by the action of a halide derived from the cyclic radical to be substituted, in the presence of triethylamine, in anhydrous medium, optionally with no solvent or in a solvent such as an amide (dimethylformamide for example) or a nitrile (acetonitrile for example) and in the presence of a palladium salt such as for example tetrakis(triphenylphosphine)palladium and copper (I) iodide, at a temperature of between 20° C. and the reflux temperature of the solvent.

When substitution with a cycloalkyl group is involved, the reaction is carried out, after protection, in the form of an acetal which may or may not be cyclic, of the ketone functional group in the alpha-position of the quinoline, by the action of an organolithium compound such as n-butyllithium or tert-butyllithium on the propargyl derivative obtained above, in anhydrous medium in an ether such as for example tetrahydrofuran at a temperature of between −78 and 0° C., followed by the action of a cycloalkanone followed by the deoxygenation of the intermediate alcohol and, finally, by the deprotection of the ketone functional group according to conventional methods.

It is understood that when the alkyl radicals represented by $R_3$ carry carboxyl or amino substituents, the latter are protected beforehand and then released after the reaction. The procedure is carried out according to customary methods which do not adversely affect the rest of the molecule, in particular according to the methods described by T. W. Greene and P. G. M. Wuts, Protective Groups in Organic Synthesis (2nd ed.), A. Wiley—Interscience Publication (1991), or by Mc Omie, Protective Groups in Organic Chemistry, Plenum Press (1973).

The protected carboxyl or carboxymethyl radical represented by $R'_2$ may be chosen from the easily hydrolyzable esters. By way of example, there may be mentioned methyl, benzyl or tert-butyl esters, or allyl or phenylpropyl esters. Where appropriate, the carboxyl radical is protected simultaneously with the reaction. In this case, the product of general formula (II) used carries a radical $R'_2$ which is a carboxyl or carboxymethyl radical.

The removal, where appropriate, of the acid-protecting radical in order to obtain a quinolylpropylpiperidine derivative for which $R_2$ is a carboxyl or carboxymethyl radical, is carried out according to usual methods, in particular by acid hydrolysis or saponification of the ester $R'_2$. he sodium hydroxide is in particular reacted in aqueous-organic medium, for example in an alcohol such as methanol or an ether such as dioxane, at a temperature of between 20° C. and the reflux temperature of the reaction mixture. Hydrolysis in aqueous hydrochloric acid at a temperature of between 20 and 100° C. can also be used.

According to the invention, the derivative of general formula (I) for which $R_2$ is hydroxymethyl can be prepared by the action of a suitable reducing agent on a derivative for which $R'_2$ is carboxyl or protected carboxyl. Before carrying out such a reduction reaction, the ketone functional group in the alpha-position of the quinoline is first protected by a suitable protecting group which sustains the reduction conditions, as described further below. Also according to the invention, the derivative of general formula (I) for which R2 is carboxymethyl can be prepared from the derivative for which R'2 is hydroxymethyl, obtained as described above, by the action thereon of a halogenating or tosylating agent, then of a cyanating agent and, finally, hydrolysis of the nitrile.

More specifically, the reduction of the carboxyl can be carried out according to usual methods which do not alter the rest of the molecule, in particular by the action of a hydride (lithiumaluminum hydride or diisobutyl aluminum hydride for example) in a solvent such as an ether (tetrahydrofuran for example) at a temperature of between 20 and 60° C. The ketone functional group in the alpha-position of the quinoline is intermediately protected and then deprotected according to conventional methods known to those skilled in the art, in particular via an acetal which may or may not be cyclic.

The reduction of the free acid can be carried out according to methods also known to those skilled in the art, for example by hydrogenation in the presence of a rhodium-based or ruthenium-based catalyst, by the action of sodium hydroboride in the presence of a Lewis acid or of lithiumaluminum hydride in ether. Preferably, the ketone functional group is, in this case, also intermediately protected.

The conversion of the hydroxymethyl radical in the 3-position of the piperidine to a carboxymethyl radical is carried out according to usual methods which do not alter the rest of the molecule, in particular by the action of a halogenating agent, such as, for example, thionyl chloride or phosphorus trichloride or phosphorus tribromide, or of a tosylating agent, and then of an alkali metal cyanide, for example potassium cyanide or sodium cyanide, to prepare the corresponding cyanomethyl derivative, followed by hydrolysis of the nitrile.

The halogenation can be carried out in a chlorinated solvent (dichloromethane or chloroform for example) at a suitable reaction temperature, which can be subambient, ambient or superambient. For example, a temperature of between 0° C. and the reflux temperature of the solvent may be employed.

According to the invention, the products of general formula (I) may also be obtained according to process B, by condensing the $R_3$ chain with the quinolylpropylpiperidine derivative (II') of general formula:

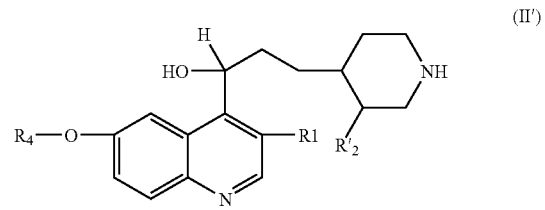

in which $R_1$ and $R_4$ are as defined above and $R'_2$ represents a protected carboxyl or carboxymethyl radical, to obtain a quinolylpropylpiperidine derivative of general formula (III'):

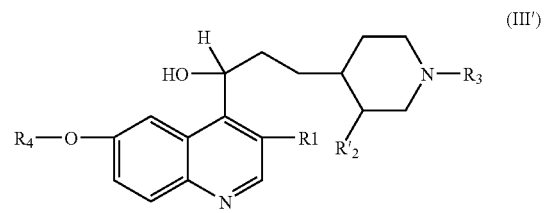

in which $R_1$, $R'_2$ and $R_4$ are as defined above and $R_3$ is as defined previously, then oxidation of the alcohol functional group in the alpha-position of the quinoline to a ketone, to obtain a derivative of formula (III) as defined above, in which $R_1$, $R'_2$ and $R_4$ are as defined above and K represents an oxygen atom, and continuation of the synthesis as described above.

The condensation of the $R_3$ chain with the piperidine is carried out under the same conditions as those described in method A.

The oxidation of the alcohol functional group to a ketone is carried out by conventional methods which do not alter the rest of the molecule, for example by oxidation according to D. Swern, J. O. C., 44, 41–48 (1979), in particular in the presence of oxalyl chloride and of dimethyl sulfoxide, where appropriate in a solvent, for example dichloromethane, at a temperature of between −60 and 20° C.

When $R_1$ is a hydrogen, the intermediate (II) and also the intermediate (II') may be prepared according to a method described in patent FR 99 11679.

The quinolylpropylpiperidine derivative of general formula (II) for which $R_1$ is a fluorine atom may be prepared by oxidation of the quinolylpropylpiperidine derivative of general formula (V):

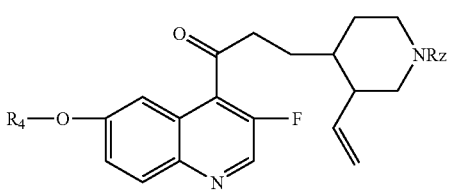

(V)

in which Rz represents an amino-protecting radical, optional protection of the carboxyl radical thus obtained, then, where appropriate, after protection of the ketone, reduction of the carboxyl radical or of the protected carboxyl radical to a hydroxymethyl radical and conversion thereof to a carboxymethyl radical as described above, protection of the latter and freeing of the ketone and of the amine.

The oxidation of the derivative of formula (V) is preferably carried out in two stages: first of all, the diol is obtained by oxidation of the vinyl group with potassium osmate dihydrate and 4-methylmorpholine N-oxide in a mixture of dichloromethane and water at a temperature of between 0° C. and the reflux temperature of the solvent, preferably at 30° C., and then the diol is oxidized with potassium permanganate and sodium metaperiodate in a mixture of acetonitrile and water at a temperature of between 0° C. and the reflux temperature of the solvent, preferably at 0° C. The protections and deprotections of the carboxyl, of the ketone and of the amine are carried out using the usual methods, where appropriate, as described above.

The reduction of the carboxyl or of the protected carboxyl and also the conversion of the hydroxymethyl to carboxymethyl are also carried out by the methods described above.

According to the invention, the quinolylpropylpiperidine derivative of general formula (V) is obtained by condensing the derivative which is lithiated in the 4-position of the quinoline (VI):

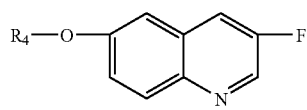

(VI)

with a piperidine derivative of general formula (VII):

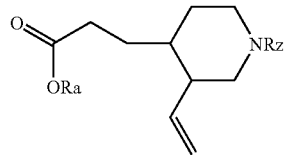

(VII)

in which Rz is an amine-protecting group defined above and Ra is an alkyl group containing from 1 to 4 carbon atoms, preferably a methyl.

The formation of the derivative which is lithiated in the 4-position of the quinoline (VI) is carried out using a strong lithiated base such as butyllithium, sec-butyllithium, or preferably lithium diisopropylamide, in a solvent such as an ether or tetrahydrofuran, at a temperature of between −78° C. and −40° C. The condensation of this lithiated derivative of quinoline with the ester (VII) is carried out in the same solvent, at a temperature of between −78° C. and 0° C.

The quinoline derivative (VI) may be prepared according to the method described in patent application WO 200240474.

The piperidine derivative of general formula (VII) may be prepared by Beckmann rearrangement of the oxime (VIII)

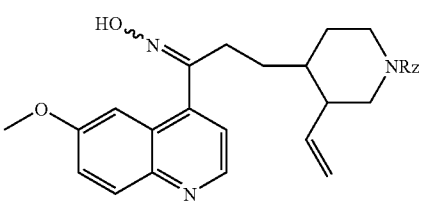

(VIII)

followed by cleavage of the amide thus obtained to acid, then esterification of this acid by conventional methods described in the literature.

The Beckmann rearrangement of the oxime (VIII) to amide can be carried out according to the methods described in the literature (M. Smith, J. March, Advanced Organic Chemistry, 5th edition, p. 1415) for example by reaction of a sulfonic acid chloride (such as para-toluene sulfonyl chloride) with the oxime in a solvent such as aqueous acetone or dichloromethane in the presence of a base such as aqueous sodium hydroxide or potassium hydroxide or an amine such as triethylamine or diisopropylethylamine for example, at a temperature of between 20° C. and the reflux temperature of the solvent.

The cleavage of the amide, produced by the Beckmann rearrangement, to acid can be carried out according to conventional methods of the literature, such as basic hydrolysis with sodium hydroxide or potassium hydroxide, or else, for example, by treatment of the amide with di-tert-butyl dicarbonate in dichloromethane in the presence of triethylamine and of 4-dimethylaminopyridine, followed by treatment with lithium hydroxide monohydrate and an aqueous solution of hydrogen peroxide using tetrahydrofuran as solvent for example.

The oxime (VIII) may be obtained from the quinolylpropylpiperidine derivative of general formula (IX):

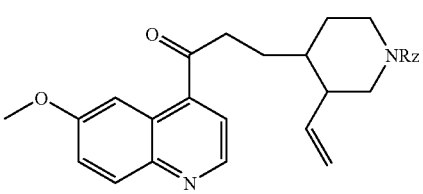

(IX)

by reaction with hydroxylamine hydrochloride in pyridine or else in a mixture of water and alcohol, such as methanol, in the presence of a base such as sodium acetate for example.

The quinolylpropylpiperidine derivative of general formula (IX) may be prepared using the method described in patent application FR 2354771.

When $R_1$ is a fluorine and $R'_2$ is a carboxymethyl, the quinolylpropylpiperidine derivative of general formula (II') may be prepared by oxidation in basic medium of the quinolylpropylpiperidine derivative of general formula (X):

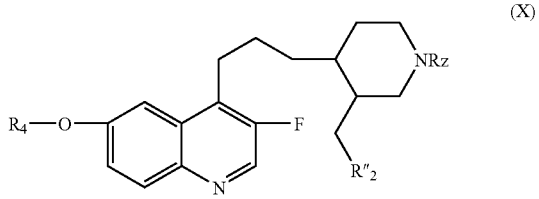

in which $R_4$ is as defined above, Rz is an amino-protecting group, and $R''_2$ is the protected carboxyl radical corresponding to $R'_2$, then deprotection of the amino. The oxidation is carried out by the action of oxygen, preferably in an inert solvent such as dimethyl sulfoxide, in the presence of tert-butanol and of a base such as potassium or sodium tert-butoxide, at a temperature of between 0 and 100° C. The deprotection of the amine functional group of the piperidine is carried out according to the conventional methods recalled above.

The quinolylpropylpiperidine derivative of general formula (X) may be prepared by selective hydrogenation of the quinolylpropylpiperidine derivative of general formula (XI):

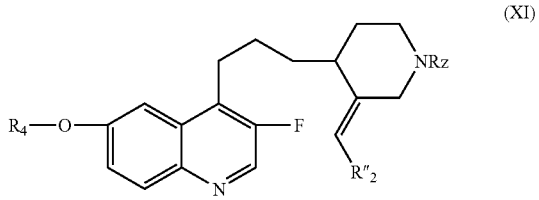

in which $R_4$, Rz and $R''_2$ are as defined above, under a pressure of 1 to 100 bar and at a temperature of between 20 and 80° C., in a solvent such as an alcohol, ethanol for example, or an amide, dimethylformamide for example, in the presence of a catalyst, for example palladium on charcoal or palladium on barium sulfate.

The protective radical is more particularly the benzyloxycarbonyl radical. In this case, the hydrogenation reaction leads directly to deprotection of the amine.

The quinolylpropylpiperidine derivative of general formula (XI) may be prepared by condensing a quinoline derivative of general formula (XII):

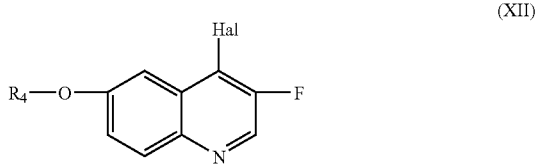

in which $R_4$ is as defined above and Hal represents an iodine or bromine atom, with a piperidine derivative of general formula (XIII):

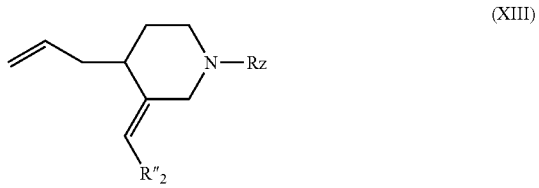

in which $R''_2$ and Rz are as defined above.

The reaction is carried out by the successive action of an organoborane (9-borabicyclo[3.3.1]nonane for example) in a solvent such as an ether (tetrahydrofuran, dioxane for example) at a temperature of between −20 and 20° C., followed by the addition of the quinoline derivative of general formula (VII), by analogy with the methods described by Suzuki et al., Pure and Appl. Chem., 57, 1749 (1985). The reaction is generally carried out in the presence of a palladium salt (palladiumdiphenylphosphinoferrocene chloride for example) and of a base such as potassium phosphate, at a temperature of between 20° C. and the reflux temperature of the solvent.

The piperidine derivative of general formula (XIII) may be prepared by the Wittig reaction, by condensing a phosphorus ylide with a piperidine derivative of general formula (XIV):

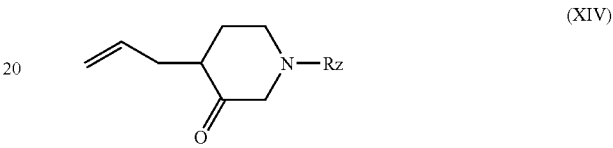

in which Rz is as defined above.

The procedure is advantageously carried out using methyl (triphenylphosphoranylidene)acetate, in a solvent such as for example toluene, at a temperature of between 20 and 110° C.

The 3-oxopiperidine derivative of general formula (XIV) may be prepared according to or by analogy with the method described by Y. Takeuchi et al., Synthesis, 10, 1814 (1999).

The quinoline derivative of general formula (XII) in which R1 represents a fluorine atom may be prepared according to the method described in patent WO 200240474-A2.

The quinolylpropylpiperidine derivative of general formula (II') for which $R'_2$ is a protected carboxyl radical may be prepared from the corresponding derivative for which $R'_2$ is a protected carboxymethyl radical, the hydroxyl in the alpha-position of the quinoline being protected, by reducing this radical to an alcohol, converting to a p-toluenesulfonyloxyethyl derivative and then converting this derivative to a vinyl derivative by an elimination reaction followed by the oxidation of the derivative obtained, and then deprotection of the alcohol functional group in the alpha-position of the quinoline and deprotection of the carboxyl radical.

The reduction of the protected acid to a hydroxyethyl radical is carried out according to the usual methods which do not adversely affect the rest of the molecule, in particular the reaction is carried out by action of a hydride, lithiumaluminum hydride or diisobutylaluminum hydride, for example, in a solvent such as an ether, for example tetrahydrofuran, at a temperature of between 20 and 60° C.

The conversion of the hydroxyethyl derivative to a para-toluenesulfonyloxyethyl derivative is carried out in particular according to the method described by L. F. Fieser and M. Fieser, Reagents for Organic Synthesis, vol. 1, 1179 (1967), using p-toluenesulfonyl chloride in the presence of a base such as a tertiary amine, for example triethylamine, or an aromatic amine, for example pyridine, in a halogenated solvent, for example dichloromethane, or without solvent, at a temperature of between 0 and 50° C.

The conversion of the p-toluenesulfonyloxyethyl derivative to a vinyl derivative is carried out by an elimination reaction, in particular according to the method described by A. Sharma et al., Org. Prep. Proced. Int., 25(3), 330–333

(1993), in the presence of a base, for example potassium t-butoxide, in a solvent, for example dimethylsulfoxide, at a temperature of between 20 and 100° C.

The conversion of the vinyl derivative to a carboxyl derivative is carried out by the oxidation methods described in the literature, in particular using sodium metaperiodate in the presence of ruthenium trichloride hydrate, in a mixture of solvents such as for example the water/acetonitrile mixture, at a temperature of between 20 and 60° C.

It is understood that the derivatives of general formula (I), but also the intermediates of formulae (II) and (II'), (III) and (III'), (V), (VIII), (IX) and (X), and also several of the corresponding starting materials, exhibit "cis/trans" isomerism at the level of the substituents in the 3- and 4-position of piperidine. The derivatives having the "trans" configuration may be obtained from the derivatives having the "cis" configuration according to or by analogy with the method described in international application WO 99/37635, or from intermediates which exist in the form of mixtures, after separation according to known methods.

The quinolylpropylpiperidine derivatives of general formula (I) may be purified, where appropriate by physical methods such as crystallization or chromatography.

Moreover, it is also understood that the compounds of general formula (I) also exist in enantiomeric and diastereoisomeric forms, which forms, and also their mixtures, fall within the context of the present invention. The latter may be, where appropriate, separated in particular by chromatography on silica or by High-Performance Liquid Chromatography (HPLC). Likewise, the cis and trans derivatives may be separated by chromatography on silica or by High-Performance Liquid Chromatography (HPLC).

The quinolylpropylpiperidine derivatives of general formula (I) may be converted to addition salts with acids, by known methods. It is understood that these salts also fall within the scope of the present invention.

As examples of addition salts with pharmaceutically acceptable acids, there may be mentioned the salts formed with inorganic acids (hydrochlorides, hydrobromides, sulfates, nitrates, phosphates) or with organic acids (succinates, fumarates, tartarates, acetates, propionates, maleates, citrates, methanesulfonates, ethanesulfonates, phenylsulfonates, p-toluenesulfonates, isethionates, naphthylsulfonates or camphorsulfonates, or with substitution derivatives of these compounds).

Some of the quinolylpropylpiperidine derivatives of general formula (I) carrying a carboxyl radical may be converted to the form of metal salts or to addition salts with the nitrogen bases according to methods known per se. These salts also fall within the scope of the present invention. The salts may be obtained by the action of a metal base (for example an alkali or alkaline-earth metal), of ammonia or of an amine, on a product according to the invention, in an appropriate solvent such as an alcohol, an ether or water, or by an exchange reaction with a salt of an organic acid. The salt formed precipitates after optional concentration of the solution, it is separated by filtration, decantation or freeze-drying. As examples of pharmaceutically acceptable salts, there may be mentioned the salts with alkali metals (sodium, potassium, lithium) or with alkaline-earth metals (magnesium, calcium), the ammonium salt, the salts of nitrogen bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine, dibenzylamine).

The quinolylpropylpiperidine derivatives according to the invention are particularly advantageous antibacterial agents.

In vitro, on gram-positive microbes, the quinolylpropylpiperidine derivatives according to the invention have proved active at concentrations of between 0.03 and 4 µg/ml on meticillin-resistant *Staphylococcus aureus* AS5155, also at concentrations of between 0.06 and 8 µg/ml on *Streptococcus pneumoniae* 6254–01 and at concentrations of between 0.06 and 64 µg/ml on *Enterococcus faecium* H983401, and on gram-negative microbes they have proved active at concentrations of between 0.12 and 32 µg/ml on *Moraxella catharrhalis* IPA152; in vivo, they have proved active on experimental infections of mice with *Straphylococcus aureus* IP8203 at doses of between 12 and 150 mg/kg by the subcutaneous route ($CD_{50}$) and for some of them at doses of between 26 and 150 mg/kg by the oral route.

Finally, the products according to the invention are particularly advantageous because of their low toxicity. None of the products exhibited toxicity at the dose of 100 mg/kg by the subcutaneous route in mice.

These properties make the products, and also their salts of pharmaceutically acceptable acids and bases, suitable for use as medicaments in the treatment of ailments involving sensitive microorganisms caused by gram (+) bacteria, and in particular in that of staphylococcic infections, such as staphylococcal septicemias, malignant staphylococcic infections of the face or skin, pyoderma, septic or suppurant wounds, anthrax, phlegmons, erysipelas, acute primary or post-influenza staphylococcic infections, bronchopneumonias or pulmonary suppurations.

These products can also be used as medicaments in the treatment of colibacilloses and related infections, in infections with proteus, with klebsiella and with salmonella, and in other ailments caused by gram (−) bacteria.

A subject of the present invention is therefore also, as medicaments, and in particular medicaments intended for the treatment of bacterial infections in humans or animals, the compounds of formula (I) as defined above, and also their pharmaceutically acceptable salts, and in particular the preferred compounds mentioned above.

The present invention also relates to the pharmaceutical compositions containing at least one quinolylpropylpiperidine derivative according to the invention, where appropriate in the form of a salt, in the pure state or in the form of a combination with one or more compatible and pharmaceutically acceptable diluents or adjuvants.

The compositions according to the invention can be used orally, parenterally, topically, rectally or as aerosols.

As solid compositions for oral administration, use may be made of tablets, pills, gelatin capsules, powders or granules. In these compositions, the active product according to the invention is mixed with one or more inert diluents or adjuvants, such as sucrose, lactose or starch. These compositions can comprise substances other than diluents, for example a lubricant such as magnesium stearate or a coating intended for controlled release.

As liquid compositions for oral administration, use may be made of pharmaceutically acceptable solutions, suspensions, emulsions, syrups and elixirs containing inert diluents such as water or paraffin oil. These compositions can also comprise substances other than diluents, for example wetting, sweetening or flavoring products.

The compositions for parenteral administration can be sterile solutions or emulsions. As a solvent or vehicle, use may be made of water, propylene glycol, a polyethylene glycol, plant oils, in particular olive oil, and injectable organic esters, for example ethyl oleate. These compositions can also contain adjuvants, in particular wetting agents, isotonicity agents, emulsifiers, dispersing agents and stabilizers.

The sterilization can be carried out in several ways, for example using a bacteriological filter, by irradiation or by heating. They can also be prepared in the form of sterile solid compositions which can be dissolved at the time of use in sterile water or any other injectable sterile medium.

The compositions for topical administration can be, for example, creams, ointments, lotions or aerosols.

The compositions for rectal administration are suppositories or rectal capsules, which contain, besides the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in serum or in any other pharmaceutically acceptable vehicle. For use in the form of dry aerosols intended to be inhaled directly, the active principle is finely divided up and combined with a water-soluble solid diluent or vehicle with a particle size of 30 to 80 μm, for example dextran, mannitol or lactose.

In human therapy, the novel quinolylpropylpiperidine derivatives according to the invention are particularly useful in the treatment of infections of bacterial origin. The doses depend on the desired effect and the duration of treatment. The physician will determine the dosage which he or she estimates to be the most suitable as a function of the treatment, as a function of age, of weight, and of the degree of the infection, and of other factors specific to the individual to be treated. Generally, the doses are between 750 mg and 3 g of active product taken in 2 or 3 doses per day orally, or between 400 mg and 1.2 g taken intravenously for an adult.

The following example illustrates a composition according to the invention.

According to the usual technique, a liquid composition intended for parenteral use is prepared, comprising:

| | |
|---|---|
| (3R,4R)-4-[3-(3-fluoro-6-methoxy-quinolin-4-yl)-3-oxopropyl]-1-[3-(2,3,5-trifluorophenylthio)prop-2-ynyl]piperidine-3-carboxylic acid | 1 g |
| glucose | qs 2.5% |
| sodium hydroxide | qs pH = 4–4.5 |
| water for injectable preparation | qs 20 ml | qs = in sufficient quantities up to

Finally, a subject of the invention is, as novel industrial products, and in particular as intermediate products required for the preparation of the products of formula (I):
the products of formula (II) as defined above, in which $R_1$ is a fluorine atom and the ketone is free or protected;
the products of formula (A):

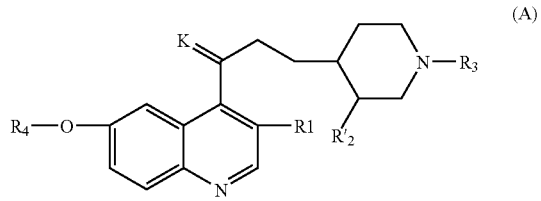

(A)

in which $R_1$, $R'_2$, $R_3$ and $R_4$ are as defined above and K represents a ketone-protecting group;

the products of formula (B):

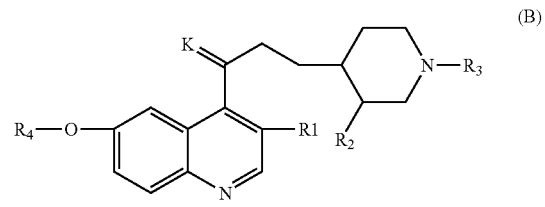

(B)

in which $R_1$, $R_2$, $R_3$ and $R_4$ are as defined above and K represents a ketone-protecting group, corresponding to products obtained at the end of various treatments carried out on the products of formula (III);
the products of formula (V) as defined above;
the products of formula (C):

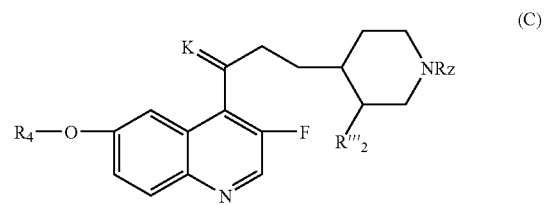

(C)

in which $R_4$, Rz and K are as defined above and $R'''_2$ represents a free or protected carboxyl or carboxymethyl radical or a hydroxymethyl radical, corresponding to products obtained at the end of the various treatments carried out on the products of formula (V);
the products of formula (VII) as defined above;
the products of formula (VIII) as defined above.

Among the products according to the invention, those which are more particularly advantageous are the quinolylpropylpiperidine derivatives mentioned below, and in particular those described in the examples, in a non-limiting manner:

(3RS,4RS) or (3SR,4RS)-4-[3-oxo-3-(6-methoxyquinolin-4-yl)propyl]-1-(2-phenylthioethyl)piperidine-3-carboxylic acid (3RS,4RS) or (3SR,4RS)-4-[3-oxo-3-(6-methoxyquinolin-4-yl)propyl]-1-[2-(3-fluorophenylthio)ethyl]-piperidine-3-carboxylic acid (3RS,4RS) or (3SR,4RS)-4-[3-oxo-3-(6-methoxyquinolin-4-yl)propyl]-1-[2-(2,5-difluorophenylthio)ethyl]-piperidine-3-carboxylic acid 3RS,4RS) or (3SR,4RS)-4-[3-oxo-3-(6-methoxyquinolin-4-yl)propyl]-1-[2-(3,5-difluorophenylthio)ethyl]-piperidine-3-carboxylic acid (3RS,4RS) or (3SR,4RS)-4-[3-oxo-3-(6-methoxyquinolin-4-yl)propyl]-1-[2-(2,3,5-trifluorophenylthio)ethyl]-piperidine-3-carboxylic acid (3RS,4RS) or (3SR,4RS)-4-[3-oxo-3-(6-methoxyquinolin-4-yl)propyl]-1-[2-(n-propylthio)ethyl]piperidine-3-carboxylic acid (3RS,4RS) or (3SR,4RS)-4-[3-oxo-3-(6-methoxyquinolin-4-yl)propyl]-1-[2-(n-butylthio)ethyl]piperidine-3-carboxylic acid (3RS,4RS) or (3SR,4RS)-4-[3-oxo-3-(6-methoxyquinolin-4-yl)propyl]-1-[2-(cyclopropylthio)ethyl]piperidine-3-carboxylic acid (3RS,4RS) or (3SR,4RS)-4-[3-oxo-3-(6-methoxyquinolin-4-yl)propyl]-1-[2-(cyclobutylthio)ethyl]piperidine-3-carboxylic acid (3RS,4RS) or (3SR,4RS)-4-[3-oxo-3-(6-methoxyquinolin-4-yl)propyl]-1-[2-(cyclopentylthio)ethyl]piperidine-3-carboxylic acid (3RS,4RS) or (3SR,4RS)-4-[3-oxo-3-(6-methoxyquinolin-4-yl)propyl]-1-[2-(cyclohexylthio)ethyl]piperidine-3-carboxylic acid (3RS,4RS) or (3SR,4RS)-4-[3-oxo-3-(6-methoxyquinolin-4-yl)propyl]-1-[2-(thien-2-yl)thioethyl]piperidine-3-carboxylic acid (3RS,4RS) or (3SR,4RS)-4-[3-oxo-3-(6-methoxyquinolin-4-yl)propyl]-1-[2-(5-fluorothien-2-yl)thioethyl]-piperidine-3-carboxylic acid (3RS,4RS) or (3SR,4RS)-4-[3-oxo-3-(6-methoxyquinolin-4-yl)propyl]-1-[2-(4-fluorothien-2-yl)thioethyl]-piperidine-3-carboxylic acid (3RS,4RS) or (3SR,4RS)-4-[3-oxo-3-(6-methoxyquinolin-4-yl)propyl]-1-[2-(3-fluorothien-2-yl)thioethyl]-piperidine-3-carboxylic acid (3RS,4RS) or (3SR,4RS)-4-[3-oxo-3-(6-methoxyquinolin-4-yl)propyl]-1-[2-(thien-3-yl)thioethyl]piperidine-3-carboxylic acid (3RS,4RS) or (3SR,4RS)-4-[3-oxo-3-(6-methoxyquinolin-4-yl)propyl]-1-[2-(1,3-thiazol-2-yl)thioethyl]-piperidine-3-carboxylic acid (3RS,4RS) or (3SR,4RS)-4-[3-oxo-3-(6-methoxyquinolin-4-yl)propyl]-1-[2-(pyridin-2-yl)thioethyl]piperidine-3-carboxylic acid (3RS,4RS) or (3SR,4RS)-4-[3-oxo-3-(6-methoxyquinolin-4-yl)propyl]-1-[2-(4-fluoropyridin-2-yl)thioethyl]-piperidine-3-carboxylic acid (3RS,4RS) or (3SR,4RS)-4-[3-oxo-3-(6-methoxyquinolin-4-yl)propyl]-1-[2-(3-fluoropyridin-2-yl)thioethyl]-piperidine-3-carboxylic acid (3RS,4RS) or (3SR,4RS)-4-[3-oxo-3-(6-methoxyquinolin-4-yl)propyl]-1-[3-fluorophenyl)prop-2-ynyl]-piperidine-3-carboxylic acid (3RS,4RS) or (3SR,4RS)-4-[3-oxo-3-(6-methoxyquinolin-4-yl)propyl]-1-[3-(2,5-difluorophenyl)prop-2-ynyl]-piperidine-3-carboxylic acid (3RS,4RS) or (3SR,4RS)-4-[3-oxo-3-(6-methoxyquinolin-4-yl)propyl]-1-[3-(3,5-difluorophenyl)prop-2-ynyl]-piperidine-3-carboxylic acid (3RS,4RS) or (3SR,4RS)-4-[3-oxo-3-(6-methoxyquinolin-4-yl)propyl]-1-[3-(2,3,5-trifluorophenyl)prop-2-ynyl]-piperidine-3-carboxylic acid (3RS,4RS) or (3SR,4RS)-4-[3-oxo-3-(6-methoxyquinolin-4-yl)propyl]-1-[3-(thien-2-yl)prop-2-ynyl]piperidine-3-carboxylic acid (3RS,4RS) or (3SR,4RS)-4-[3-oxo-3-(6-methoxyquinolin-4-yl)propyl]-1-[3-(5-fluorothien-2-yl)prop-2-ynyl]-piperidine-3-carboxylic acid (3RS,4RS) or (3SR,4RS)-4-[3-oxo-3-(6-methoxyquinolin-4-yl)propyl]-1-[3-(4-fluorothien-2-yl)prop-2-ynyl]-piperidine-3-carboxylic acid (3RS,4RS) or (3SR,4RS)-4-[3-oxo-3-(6-methoxyquinolin-4-yl)propyl]-1-[3-(3-fluorothien-2-yl)prop-2-ynyl]-piperidine-3-carboxylic acid (3RS,4RS) or (3SR,4RS)-4-[3-oxo-3-(3-fluoro-6-methoxyquinolin-4-yl)propyl]-1-(2-phenylthioethyl)-piperidine-3-carboxylic acid (3RS,4RS) or (3SR,4RS)-4-[3-oxo-3-(3-fluoro-6-methoxyquinolin-4-yl)propyl]-1-[2-(3-fluorophenylthio)ethyl]piperidine-3-carboxylic acid (3RS,4RS) or (3SR,4RS)-4-[3-oxo-3-(3-fluoro-6-methoxyquinolin-4-yl)propyl]-1-[2-(2,5-difluorophenylthio)ethyl]piperidine-3-carboxylic acid (3RS,4RS) or (3SR,4RS)-4-[3-oxo-3-(3-fluoro-6-methoxyquinolin-4-yl)propyl]-1-[2-(3,5-difluorophenylthio)ethyl]piperidine-3-carboxylic acid (3RS,4RS) or (3SR,4RS)-4-[3-oxo-3-(3-fluoro-6-methoxyquinolin-4-yl)propyl]-1-[2-(2,3,5-trifluorophenylthio)ethyl]piperidine-3-carboxylic acid (3RS,4RS) or (3SR,4RS)-4-[3-oxo-3-(3-fluoro-6-methoxyquinolin-4-yl)propyl]-1-[2-(n-proplthio)-ethyl]piperidine-3-carboxylic acid (3RS,4RS) or (3SR,4RS)-4-[3-oxo-3-(3-fluoro-6-methoxyquinolin-4-yl)propyl]-1-[2-(n-butylthio)-ethyl]piperidine-3-carboxylic acid (3RS,4RS) or (3SR,4RS)-4-[3-oxo-3-(3-fluoro-6-methoxyquinolin-4-yl)propyl]-1-[2-(cyclopropylthio)ethyl]piperidine-3-carboxylic acid (3RS,4RS) or (3SR,4RS)-4-[3-oxo-3-(3-fluoro-6-methoxyquinolin-4-yl)propyl]-1-[2-(cyclobutylthio)ethyl]piperidine-3-carboxylic acid (3RS,4RS) or (3SR,4RS)-4-[3-oxo-3-(3-fluoro-6-methoxyquinolin-4-yl)propyl]-1-[2-(cyclopentylthio)ethyl]piperidine-3-carboxylic acid (3RS,4RS) or (3SR,4RS)-4-[3-oxo-3-(3-fluoro-6-methoxyquinolin-4-yl)propyl]-1-[2-(cyclohexylthio)ethyl]piperidine-3-carboxylic acid (3RS,4RS) or (3SR,4RS)-4-[3-oxo-3-(3-fluoro-6-methoxyquinolin-4-yl)propyl]-1-[2-(thien-2-yl)thioethyl]piperidine-3-carboxylic acid (3RS,4RS) or (3SR,4RS)-4-[3-oxo-3-(3-fluoro-6-methoxyquinolin-4-yl)propyl]-1-[2-(5-fluorothien-2-yl)thioethyl]piperidine-3-carboxylic acid (3RS,4RS) or (3SR,4RS)-4-[3-oxo-3-(3-fluoro-6-methoxyquinolin-4-yl)propyl]-1-[2-(4-fluorothien-2-yl)thioethyl]piperidine-3-carboxylic acid (3RS,4RS) or (3SR,4RS)-4-[3-oxo-3-(3-fluoro-6-methoxyquinolin-4-yl)propyl]-1-[2-(3-flourothien-2-yl)thioethyl]piperidine-3-carboxylic acid (3RS,4RS) or (3SR,4RS)-4-[3-oxo-3-(3-fluoro-6-methoxyquinolin-4-yl)propyl]-1-[2-(thien-3-yl)-thioethyl]piperidine-3-carboxylic acid (3RS,4RS) or (3SR,4RS)-4-[3-oxo-3-(3-fluoro-6-methoxyquinolin-4-yl)propyl]-1-[2-(1,3-thiazol-2-yl)thioethyl]piperidine-3-carboxylic acid (3RS,4RS) or (3SR,4RS)-4-[3-oxo-3-(3-fluoro-6-methoxyquinolin-4-yl)propyl]-1-[2-(pyridin-2-yl)-thioethyl]piperidine-3-carboxylic acid (3RS,4RS) or (3SR,4RS)-4-[3-oxo-3-(3-fluoro-6-methoxyquinolin-4-yl)propyl]-1-[2-(4-fluoropyridin-2-yl)thioethyl]piperidine-3-carboxylic acid (3RS,4RS) or (3SR,4RS)-4-[3-oxo-3-(3-fluoro-6-methoxyquinolin-4-yl)propyl]-1-[2-(3-fluoropyridin-2-yl)thioethyl]piperidine-3-carboxylic acid (3RS,4RS) or (3SR,4RS)-4-[3-oxo-3-(3-fluoro-6-methoxyquinolin-4-yl)propyl]-1-[3-(3-fluorophenyl)-prop-2-ynyl]piperidine-3-carboxylic acid (3RS,4RS) or (3SR,4RS)-4-[3-oxo-3-(3-fluoro-6-methoxyquinolin-4-yl)propyl]-1-[3-(2,5-difluorophenyl)prop-2-ynyl]piperidine-3-carboxylic acid (3RS,4RS) or (3SR,4RS)-4-[3-oxo-3-(3-fluoro-6-methoxyquinolin-4-yl)propyl]-1-[3-(3,5-difluorophenyl)prop-2-ynyl]piperidine-3-carboxylic acid (3RS,4RS) or (3SR,4RS)-4-[3-oxo-3-(3-fluoro-6-methoxyquinolin-4-yl)propyl]-1-[3-(2,3,5-trifluorophenyl)prop-2-ynyl]piperidine-3-carboxylic acid (3RS,4RS) or (3SR,4RS)-4-[3-oxo-3-(3-fluoro-6-methoxyquinolin-4-yl)propyl]-1-[3-(thien-2-yl)prop-2-ynyl]piperidine-3-carboxylic acid (3RS,4RS) or (3SR,4RS)-4-[3-oxo-3-(3-fluoro-6-methoxyquinolin-4-yl)propyl]-1-[3-(5-fluorothien-2-yl)prop-2-ynyl]piperidine-3-carboxylic acid (3RS,4RS) or (3SR,4RS)-4-[3-oxo-3-(3-fluoro-6-methoxyquinolin-4-yl)propyl]-1-[3-(4-fluorothien-2-yl)prop-2-ynyl]piperidine-3-carboxylic acid (3RS,4RS) or (3SR,4RS)-4-[3-oxo-3-(3-fluoro-6-methoxyquinolin-4-yl)propyl]-1-[3-(3-fluorothien-2-yl)prop-2-ynyl]piperidine-3-carboxylic acid (3RS,4RS) or (3SR,4RS)-4-[3-oxo-3-(3-fluoro-6-methoxyquinolin-4-yl)propyl]-1-[3-(thien-3-yl)prop-2-ynyl]piperidine-3-carboxylic acid (3RS,4RS) or (3SR,4RS)-4-[3-oxo-3-(6-methoxyquinolin-4-yl)propyl]-1-(2-phenylthioethyl)piperidine-3-acetic acid (3RS,4RS) or (3SR,4RS)-4-[3-oxo-3-(6-methoxyquinolin-4-yl)propyl]-1-[2-(3-fluorophenylthio)ethyl]-piperidine-3-acetic acid (3RS,4RS) or (3SR,4RS)-4-[3-oxo-3-(6-methoxyquinolin-4-yl)propyl]-1-[2-(2,5-difluorophenylthio)ethyl]-piperidine-3-acetic acid (3RS,4RS) or (3SR,4RS)-4-[3-oxo-3-(6-methoxyquinolin-4-yl)propyl]-1-[2-(3,5-difluorophenylthio)ethyl]-piperidine-3-acetic acid (3RS,4RS) or (3SR,4RS)-4-[3-oxo-3-(6-methoxyquinolin-4-yl)propyl]-1-[2-(2,3,5-trifluorophenylthio)ethyl]-piperidine-3-acetic acid (3RS,4RS) or (3SR,4RS)-4-[3-oxo-3-(6-methoxyquinolin-4-yl)propyl]-1-[2-(n-propylthio)ethyl]piperidine-3-acetic acid (3RS,4RS) or (3SR,4RS)-4-[3-oxo-3-(6-methoxyquinolin-4-yl)propyl]-1-[2-(n-propylthio)ethyl]piperidine-3-acetic acid (3RS,4RS) or (3SR,4RS)-4-[3-oxo-3-(6-methoxyquinolin-4-yl)propyl]-1-[2-(cyclopropylthio)ethyl]piperidine-3-acetic acid (3RS,4RS) or (3SR,4RS)-4-[3-oxo-3-(6-methoxyquinolin-4-yl)propyl]-1-[2-(cyclobutylthio)ethyl]piperidine-3-acetic acid (3RS,4RS) or (3SR,4RS)-4-[3-oxo-3-(6-methoxyquinolin-4-yl)propyl]-1-[2-(cyclopentylthio)ethyl]piperidine-3-acetic acid (3RS,4RS) or (3SR,4RS)-4-[3-oxo-3-(6-methoxyquinolin-4-yl)propyl]-1-[2-(cyclohexylthio)ethyl]piperidine-3-acetic acid (3RS,4RS) or (3SR,4RS)-4-[3-oxo-3-(6-methoxyquinolin-4-yl)propyl]-1-[2-(thien-2-yl)thioethyl]piperidine-3-acetic acid (3RS,4RS) or (3SR,4RS)-4-[3-oxo-3-(6-methoxyquinolin-4-yl)propyl]-1-[2-(5-fluorothien-2-yl)thioethyl]-piperidine-3-acetic acid (3RS,4RS) or (3SR,4RS)-4-[3-oxo-3-(6-methoxyquinolin-4-yl)propyl]-1-[2-(4-fluorothien-2-yl)thioethyl]-piperidine-3-acetic acid (3RS,4RS) or (3SR,4RS)-4-[3-oxo-3-(6-methoxyquinolin-4-yl)propyl]-1-[2-(3-fluorothien-2-yl)thioethyl]-piperidine-3-acetic acid (3RS,4RS) or (3SR,4RS)-4-[3-oxo-3-(6-methoxyquinolin-4-yl)propyl]-1-[2-(thien-3-yl)thioethyl]piperidine-3-acetic acid (3RS,4RS) or (3SR,4RS)-4-[3-oxo-3-(6-methoxyquinolin-4-yl)propyl]-1-[2-(1,3-thiazol-2-yl)thioethyl]-piperidine-3-acetic acid (3RS,4RS) or (3SR,4RS)-4-[3-oxo-3-(6-methoxyquinolin-4-yl)propyl]-1-[2-(pyridin-2-yl)thioethyl]piperidine-3-acetic acid (3RS,4RS) or (3SR,4RS)-4-[3-oxo-3-(6-methoxyquinolin-4-yl)propyl]-1-[2-(4-fluoropyridin-2-yl)thioethyl]-piperidine-3-acetic acid (3RS,4RS) or (3SR,4RS)-4-[3-oxo-3-(6-methoxyquinolin-4-yl)propyl]-1-[2-(3-fluoropyridin-2-yl)thioethyl]-piperidine-3-acetic acid (3RS,4RS) or (3SR,4RS)-4-[3-oxo-3-(6-methoxyquinolin-4-yl)propyl]-1-[3-(3-fluorophenyl)prop-2-ynyl]-piperidine-3-acetic acid (3RS,4RS) or (3SR,4RS)-4-[3-oxo-3-(6-methoxyquinolin-4-yl)propyl]-1-[3-(2,5-difluorophenyl)prop-2-ynyl]-piperidine-3-acetic acid (3RS,4RS) or (3SR,4RS)-4-[3-oxo-3-(6-methoxyquinolin-4-yl)propyl]-1-[3-(3,5-difluorophenyl)prop-2-ynyl]-piperidine-3-acetic acid (3RS,4RS) or (3SR,4RS)-4-[3-oxo-3-(6-methoxyquinolin-4-yl)propyl]-1-[3-(2,3,5-trifluorophenyl)prop-2-ynyl]piperidine-3-acetic acid (3RS,4RS) or (3SR,4RS)-4-[3-oxo-3-(6-methoxyquinolin-4-yl)propyl]-1-[3-(thien-2-yl)prop-2-ynyl]piperidine-3-acetic acid (3RS,4RS) or (3SR,4RS)-4-[3-oxo-3-(6-methoxyquinolin-4-yl)propyl]-1-[3-(5-fluorothien-2-yl)prop-2-ynyl]-piperidine-3-acetic acid (3RS,4RS) or (3SR,4RS)-4-[3-oxo-3-(6-methoxyquinolin-4-yl)propyl]-1-[3-(4-fluorothien-2-yl)prop-2-ynyl]-piperidine-3-acetic acid (3RS,4RS) or (3SR,4RS)-4-[3-oxo-3-(6-methoxyquinolin-4-yl)propyl]-1-[3-(3-fluorothien-2-yl)prop-2-ynyl]-piperidine-3-acetic acid (3RS,4RS) or (3SR,4RS)-4-[3-oxo-3-(6-methoxyquinolin-4-yl)propyl]-1-[3-(thien-3-yl)prop-2-ynyl]piperidine-3-acetic acid

EXAMPLE 1

(3R,4R)-1-(2-Cyclohexylsulfanylethyl)-4-[3-(3-fluoro-6-methoxyquinolin-4-yl)-3-oxopropyl]piperidine-3-carboxylic acid A solution of 0.084 g (0.163 mmol) of methyl (3R,4R)-1-(2-cyclohexylsulfanylethyl)-4-[3-(3-fluoro-6-methoxyquinolin-4-yl)-3-oxopropyl]piperidine-3-carboxylate in 4.5 cm³ of 5N hydrochloric acid is heated at a temperature in the region of 80° C. for 5 hours. After the heating has been stopped and the mixture has returned to ambient temperature, 10 cm³ of $CH_2Cl_2$ and 5 cm³ of water are successively added. A 5N aqueous sodium hydroxide solution is then added, followed by a 1N solution, in order to adjust the pH of the aqueous phase to a value in the region of 8. The organic phase is separated after settling out and the aqueous phase is then extracted with two times 15 cm³ of $CH_2Cl_2$. The organic phases are combined, dried over anhydrous magnesium sulfate, filtered, and concentrated to dryness under reduced pressure (2.7 kPa) to give 0.073 g of an orange oil which is purified by flash chromatography [eluent: dichloromethane/methanol/acetonitrile (92/4/4 by volume)]. After concentrating the fractions under reduced pressure, 0.03 g of (3R,4R)-1-(2-cyclohexylsulfanylethyl)-4-[3-(3-fluoro-6-methoxyquinolin-4-yl)-3-oxopropyl]piperidine-3-carboxylic acid, in the form of a yellow oil, is obtained.

$^1$H NMR spectrum (300 MHz, $(CD_3)_2SO$ d6, δ in ppm): 1.25 (mt: 5H); from 1.50 to 1.98 (mt: 10H); 2.28 (mt: 1H); 2.42 (d, J=12 Hz: 1H); from 2.50 to 2.80 (mt: 6H); 2.88 (mt: 1H); 3.06 (broad t: 1H); 3.15 (mt: 2H); 3.92 (s: 3H); 7.10 (d, J=3 Hz: 1H); 7.50 (dd, J=9 and 3 Hz: 1H); 8.05 (d, J=9 Hz: 1H); 8.90 (s: 1H). MS (EI) spectrum m/z 503 (M+H)+

The methyl (3R,4R)-1-(2-cyclohexylsulfanylethyl)-4-[3-(3-fluoro-6-methoxyquinolin-4-yl)-3-oxopropyl]-piperidine-3-carboxylate may be prepared in the following way:

1.66 g of potassium carbonate, 0.665 g of potassium iodide and then a solution of 0.738 g of 2-chloroethyl-cyclohexyl sulfide in 10 cm$^3$ of acetonitrile are added, at a temperature in the region of 20° C., under an argon atmosphere, to 1.5 g (4 mmol) of methyl (3R,4R)-4-[3-(3-fluoro-6-methoxyquinolin-4-yl)-3-oxopropyl]piperidine-3-carboxylate in solution in 20 cm$^3$ of acetonitrile and 0.8 cm$^3$ of dimethylformamide. After stirring for 16 hours at reflux and cooling the reaction mixture, 20 cm$^3$ of water are added and the mixture is then concentrated to dryness under reduced pressure (2.7 kPa). The residue is taken up with 70 cm$^3$ of CH$_2$Cl$_2$, and washed with 2 times 35 cm$^3$ of water then 40 cm$^3$ of a saturated aqueous sodium chloride solution. The organic phase is dried over anhydrous magnesium sulfate, filtered, and concentrated to dryness under reduced pressure (2.7 kPa) to give 2.2 g of an orange oil which is purified by flash chromatography [eluent: dichloromethane/methanol/acetonitrile (98/1/1 by volume)]. After concentrating tie fractions under reduced pressure, 0.67 g of an orange oil is obtained, which is purified by flash chromatography [eluent: dichloromethane/methanol/acetonitrile (98/2/2 by volume)]. After concentrating the fractions under reduced pressure, 0.495 g of methyl (3R,4R)-1-(2-cyclohexylsulfanylethyl)-4-[3-(3-fluoro-6-methoxyquinolin-4-yl)-3-oxopropyl]piperidine-3-carboxylate, in the form of an orange oil, is obtained.

MS (EI) spectrum m/z 516 (M+.) m/z 387 (base peak)

The methyl (3R,4R)-4-[3-(3-fluoro-6-methoxyquinolin-4-yl)-3-oxopropyl]piperidine-3-carboxylate may be prepared in the following way:

9 cm$^3$ of a 4N solution of hydrochloric acid in ethyl acetate and 10 cm$^3$ of MeOH are added, at a temperature in the region of 20° C., to 4 g (7.23 mmol) of methyl (3R,4R)-1-tert-butyloxycarbonyl-4-[3-(3-fluoro-6-methoxyquinolin-4-yl)-3-oxopropyl]piperidine-3-carboxylate in solution in 20 cm$^3$ of ethyl acetate. After stirring for 4 hours at a temperature in the region of 20° C., the reaction mixture is diluted with 25 cm$^3$ of ethyl acetate and a 5N aqueous sodium hydroxide solution is then added in order to adjust the pH of the aqueous phase to a value of between 8 and 8.5. The organic phase is separated after settling out and the aqueous phase is then extracted with 3 times 40 cm$^3$ of ethyl acetate. The organic phases are pooled, washed with 2 times 50 cm$^3$ of a saturated aqueous sodium chloride solution, dried over anhydrous magnesium sulfate, filtered, and concentrated to dryness under reduced pressure (2.7 kPa) to give 2.33 g of methyl (3R,4R)-4-[3-(3-fluoro-6-methoxyquinolin-4-yl)-3-oxopropyl]-piperidine-3-carboxylate in the form of an orange oil.

MS (EI) spectrum m/z 374, (M+.)

The methyl (3R,4R)-1-tert-butyloxycarbonyl-4-[3-(3-fluoro-6-methoxyquinolin-4-yl)-3-oxopropyl]-piperidine-3-carboxylate may be prepared in the following way:

1.58 cm$^3$ of a thionyl chloride solution are added, at a temperature in the region of 20° C., under an argon atmosphere, to 3.33 g (7.23 mmol) of (3R,4R)-1-tertbutyloxycarbonyl-4-[3-(3-fluoro-6-methoxyquinolin-4-yl)-3-oxo-propyl]piperidine-3-carboxylic acid in solution in 150 cm$^3$ of dichloromethane. After stirring for 1 hour at a temperature in the region of 20° C., the reaction mixture is poured over a solution of 10.55 cm$^3$ of N,N-diisopropylethylamine in 150 cm$^3$ of methanol. After stirring for 16 hours at a temperature in the region of 20° C., the reaction mixture is concentrated to dryness under reduced pressure (2.7 kPa). The residue is taken up with 150 cm$^3$ of CH$_2$Cl$_2$, and washed with 3 times 50 cm$^3$ of water and then 50 cm$^3$ of a saturated aqueous sodium chloride solution. The organic phase is dried over anhydrous magnesium sulfate, filtered, and concentrated to dryness under reduced pressure (2.7 kPa) to give 4 g of methyl (3R,4R)-1-tert-butyloxycarbonyl-4-[3-(3-fluoro-6-methoxyquinolin-4-yl)-3-oxopropyl]piperidine-3-carboxylate in the form of an orange oil.

MS (IC) spectrum m/z 475, (M+H)+

The (3R,4R)-1-tert-butyloxycarbonyl-4-[3-(3-fluoro-6-methoxyquinolin-4-yl)-3-oxopropyl]piperidine-3-carboxylic acid may be prepared in the following way:

0.147 g of potassium permanganate and then a solution of 4.15 g of sodium metaperiodate in 16 cm$^3$ of acetonitrile and 26 cm$^3$ of water are added successively, at a temperature in the region of 0° C. under an argon atmosphere, to 3.7 g (7.76 mmol) of (3R,4R)-1-tert-butyloxycarbonyl-3-(1RS,2-dihydroxyethyl)-4-[3-(3-fluoro-6-methoxyquinolin-4-yl)-3-oxopropyl]piperidine in solution in 200 cm$^3$ of acetonitrile and 5 cm$^3$ of water. After stirring for 2 hours at a temperature in the region of 0° C., 100 cm$^3$ of a saturated aqueous sodium sulfite solution are added. After stirring for 2 hours at a temperature in the region of 20° C., the reaction medium is filtered over Celite® through a sintered glass funnel. The Celite® is rinsed with 2 times 20 cm$^3$ of acetonitrile. The pH of the filtrate is adjusted to a value of between 4 and 5 by adding acetic acid. The filtrate is then concentrated to dryness under reduced pressure (2.7 kPa). The residue is taken up with 150 cm$^3$ of CH$_2$Cl$_2$, and washed with 2 times 50 cm$^3$ of water then 75 cm$^3$ of a saturated aqueous sodium chloride solution. The organic phase is dried over anhydrous magnesium sulfate, filtered, and concentrated to dryness under reduced pressure (2.7 kPa) to give 3.33 g of (3R,4R)-1-tert-butyloxycarbonyl-4-[3-(3-fluoro-6-methoxyquinolin-4-yl)-3-oxo-propyl]piperidine-3-carboxylic acid in the form of a yellow foam.

MS (IC) spectrum m/z 461, (M+H)+

The (3R,4R)-1-tert-butyloxycarbonyl-3-(1RS,2-dihydroxyethyl)-4-[3-(3-fluoro-6-methoxyquinolin-4-yl)-3-oxopropyl]piperidine may be prepared in the following way:

1.3 g of 4-methylmorpholine N-oxide and then 0.0562 g of potassium osmate dihydrate are added successively, at a temperature in the region of 30° C., under an argon atmosphere, to 2.47 g (5.02 mmol) of (3R,4R)-1-tertbutyloxycarbonyl-4-[3-(3-fluoro-6-methoxyquinolin-4-yl)-3-oxopropyl]-3-vinylpiperidine in solution in 56.2 cm$^3$ of dichloromethane and 1.25 cm$^3$ of water. After stirring for 15 hours at a temperature in the region of 30° C., 100 cm$^3$ of a saturated aqueous sodium sulfite solution are added. After stirring for 10 minutes at a temperature in the region of 20° C., the organic phase is separated after settling out and then filtered over Celite® through a sintered glass funnel. The Celite® is rinsed with 2 times 10 cm$^3$ of dichloromethane. The pH of the filtrate is adjusted to a value in the region of 7 by adding acetic acid. The filtrate is then washed with 2 times 20 cm$^3$ of a saturated aqueous sodium chloride solution. The organic phase is dried over anhydrous magnesium sulfate, filtered, and concentrated to dryness under reduced pressure (2.7 kPa) to give 3.1 g of an orange oil which is purified by flash chromatography [eluent: dichloromethane/methanol/acetonitrile (98/2/2 by volume)]. After concentrating the fractions under reduced pressure, 1.9 g of (3R,4R)-1-tert-butyloxycarbonyl-3-(1RS,2-dihydroxyethyl)-4-[3-(3-fluoro-6-methoxyquinolin-4-yl)-3-oxopropyl]-piperidine, in the form of a yellow oil, are obtained.

MS (IC) spectrum m/z 477, (M+H)+

The (3R,4R)-1-tert-butyloxycarbonyl-4-[3-(3-fluoro-6-methoxyquinolin-4-yl)-3-oxopropyl]-3-vinylpiperidine may be prepared in the following way:

15.9 cm³ of a solution of 1.6M n-butyl lithium (nBuLi)/hexane are added, at a temperature in the region of −78° C., under an argon atmosphere, to 3.57 cm³ (25.4 mmol) of diisopropylamine in solution in 20 cm³ of tetrahydrofuran. After returning to a temperature in the region of 0° C. for a period of 10 minutes, the reaction medium is again cooled to a temperature in the region of −78° C. A solution of 2.97 g (16.8 mmol) of 3-fluoro-6-methoxyquinoline in 40 cm³ of tetrahydrofuran is then added under an argon atmosphere. After stirring for 4 hours at a temperature in the region of −78° C. and then returning to a temperature in the region of −40° C., a solution of 6 g (17.6 mmol) of (3R,4R)-1-tert-butyloxycarbonyl-4-(2-methoxycarbonylethyl)-3-vinylpiperidine in 40 cm³ of tetrahydrofuran is added under an argon atmosphere. After stirring for 10 minutes at a temperature in the region of −40° C. and then returning in 10 minutes to a temperature in the region of −10° C., 30 cm³ of a saturated aqueous solution with ammonium chloride, 30 cm³ of ethyl acetate and 30 cm³ of water are successively added. The organic phase is separated after settling out, washed successively with 2 times 40 cm³ of water and 40 cm³ of a saturated aqueous sodium chloride solution, dried over anhydrous magnesium sulfate, filtered, and concentrated to dryness under reduced pressure (2.7 kPa) to give 8 g of an orange oil which is purified by flash chromatography (eluent: dichloromethane/methanol/acetonitrile (100/0/0 then 99/0.5/0.5 by volume)]. After concentrating the fractions under reduced pressure, 2.47 g of (3R,4R)-1-tert-butyloxycarbonyl-4-[3-(3-fluoro-6-methoxyquinolin-4-yl)-3-oxopropyl]-3-vinylpiperidine, in the form of a yellow oil, are obtained.

MS (IC) spectrum m/z 443, (M+H)+

The (3R,4R)-1-tert-butyloxycarbonyl-4-(2-methoxycarbonylethyl)-3-vinyl-piperidine may be prepared in the following way:

50 cm³ of a solution of 2M trimethylsilyldiazomethane/hexane are added, at a temperature in the region of 15° C., under an argon atmosphere, to 5 g (17.64 mmol) of (3R,4R)-1-tert-butyloxycarbonyl-4-(2-carboxyethyl)-3-vinylpiperidine in solution in 50 cm³ of methanol. After stirring for 3 hours at a temperature in the region of 22° C., the reaction medium is concentrated to dryness under reduced pressure (2.7 kPa) to give 5.3 g of (3R,4R)-1-tert-butyloxycarbonyl-4-(2-methoxycarbonylethyl)-3-vinylpiperidine in the form of an orange oil.

MS (EI) spectrum m/z 297 (M+.) m/z 57 (base peak)

The (3R,4R)-1-tert-butyloxycarbonyl-4-(2-carboxyethyl)-3-vinylpiperidine may be prepared in the following way:

2.26 cm³ of an aqueous solution of hydrogen peroxide at 9.8 mol/l and 0.310 g of lithium hydroxide monohydrate are added successively, at a temperature in the region of 20° C., under an argon atmosphere, to 2 g (3.7 mmol) of (3R,4R)-1-tert-butyloxycarbonyl-4-{3-[tert-butyloxycarbonyl-(6-methoxyquinolin-4-yl)amino]-3-oxopropyl}-3-vinylpiperidine in solution in 56 cm³ of tetrahydrofuran and 18 cm³ of water. After stirring for 16 hours, 50 cm³ of a saturated aqueous sodium sulfite solution are added and the tetrahydrofuran is then evaporated off under reduced pressure (2.7 kPa). The aqueous phase is filtered and the residue is washed with 3 times 30 cm³ of water. The filtrates are pooled, acidified to a pH in the region of 3.5 by adding acetic acid and then extracted with 3 times 40 cm³ of dichloromethane. The organic phases are pooled, dried over anhydrous magnesium sulfate, filtered, and concentrated to dryness under reduced pressure (2.7 kPa) to give 0.9 g of (3R,4R)-1-tert-butyloxycarbonyl-4-(2-carboxyethyl)-3-vinylpiperidine in the form of a colorless oil.

MS (IC) spectrum m/z 284, (M+H)+ m/z 301, (M+NH4)+

The (3R,4R)-1-tert-butyloxycarbonyl-4-{3-[tert-butyloxycarbonyl-(6-methoxyquinolin-4-yl)amino]-3-oxopropyl}-3-vinylpiperidine may be prepared in the following way:

1.85 cm³ of triethylamine, 11.5 g of di-tert-butyl dicarbonate and 1.61 g of 4-(dimethylamino)pyridine are added successively, at a temperature in the region of 20° C., under an argon atmosphere, to 5.8 g (13.21 mmol) of (3R,4R)-1-tert-butyloxycarbonyl-4-[3-(6-methoxyquinolin-4-ylamino)-3-oxopropyl]-3-vinylpiperidine in solution in 150 cm³ of dichloromethane. After stirring for 16 hours, the reaction medium is washed successively with 2 times 200 cm³ of water then 2 times 200 cm³ of a saturated aqueous ammonium chloride solution. The organic phase is dried over anhydrous magnesium sulfate, filtered, and concentrated to dryness under reduced pressure (2.7 kPa) to give 8.2 g of (3R,4R)-1-tert-butyloxycarbonyl-4-{3-[tert-butyloxycarbonyl-(6-methoxyquinolin-4-yl)amino]-3-oxopropyl}-3-vinylpiperidine in the form of an orange oil.

MS (IC) spectrum m/z 540, (M+H)+

The (3R,4R)-1-tert-butyloxycarbonyl-4-[3-(6-methoxyquinolin-4-ylamino)-3-oxopropyl]-3-vinylpiperidine may be prepared in the following way:

1.73 g of p-toluenesulfonyl chloride and then a solution of 0.322 g of potassium hydroxide in 4.5 cm³ of water are added successively, at a temperature in the region of 20° C., under an argon atmosphere, to 2.5 g (5.69 mmol) of (3R,4R)-1-tert-butyloxycarbonyl-4-[3-[(E,Z)-hydroxyamino]-3-(6-methoxyquinolin-4-yl)-propyl]-3-vinylpiperidine in solution in 12.75 cm³ of acetone. After stirring for 30 minutes at reflux, the reaction medium is concentrated to dryness under reduced pressure (2.7 kPa). The residue is taken up with 100 cm³ of CH₂Cl₂ and then washed with 3 times 50 cm³ of water. The organic phase is dried over anhydrous magnesium sulfate, filtered, and concentrated to dryness under reduced pressure (2.7 kPa) to give 3.2 g of an orange solid which is purified by flash chromatography [eluent: dichloromethane/methanol/acetonitrile (96/2/2 by volume)]. After concentrating the fractions under reduced pressure, 1 g of (3R,4R)-1-tert-butyloxycarbonyl-4-[3-(6-methoxyquinolin-4-yl-amino)-3-oxopropyl]-3-vinylpiperidine, in the form of a beige solid, is obtained.

MS (IC) spectrum m/z 440, (M+H)+

The (3R,4R)-1-tert-butyloxycarbonyl-4-[3-[(E,Z)-hydroxyamino]-3-(6-methoxyquinolin-4-yl)propyl]-3-vinylpiperidine may be prepared in the following way:

1.2 g of hydroxylamine hydrochloride and then 2.35 g of sodium acetate trihydrate are added successively, at a temperature in the region of 20° C., to 6.4 g (13.85 mmol) of (3R,4R)-1-tert-butyloxycarbonyl-4-[3-(6-methoxyquinolin-4-yl)-3-oxopropyl]-3-vinylpiperidine in solution in 5 cm³ of methanol and 75 cm³ of water. After stirring for 72 hours, the reaction medium is extracted with 100 cm³ then 2 times 50 cm³ of dichloromethane. The organic phases are pooled, washed with 100 cm³ of water, dried over anhydrous magnesium sulfate, filtered, and concentrated to dryness under reduced pressure (2.7 kPa) to give 5.9 g of (3R,4R)-1-tert-butyloxycarbonyl-4-[3-[(E,Z)-hydroxyamino]-3-(6-methoxyquinolin-4-yl)propyl]-3-vinylpiperidine, in the form of an orange solid.

MS (IC) spectrum m/z 440, (M+H)+

The (3R,4R)-1-tert-butyloxycarbonyl-4-[3-(6-methoxyquinolin-4-yl)-3-oxopropyl]-3-vinylpiperidine may be prepared in the following way:

4.28 cm³ of triethylamine and then a solution of 3.43 g of di-tert-butyl dicarbonate in 50 cm³ of dichloromethane are added successively, at a temperature in the region of 20° C., under an argon atmosphere, to 5 g (13.85 mmol) of (3R,4R)-4-[3-(6-methoxyquinolin-4-yl)-3-oxopropyl]-3-vinylpiperidine in solution in 100 cm³ of dichloromethane. After stirring for 16 hours, the reaction medium is washed with 3 times 150 cm³ of water. The organic phase is dried over anhydrous magnesium sulfate, filtered, and concentrated to dryness under reduced pressure (2.7 kPa) to give 6.4 g of (3R,4R)-1-tert-butyloxycarbonyl-4-[3-(6-methoxyquinolin-4-yl)-3-oxopropyl]-3-vinylpiperidine in the form of an orange oil.

MS (IC) spectrum m/z 425, (M+H)+

The (3R,4R)-4-[3-(6-methoxyquinolin-4-yl)-3-oxopropyl]-3-vinylpiperidine may be prepared using the method described in patent application FR 2354771.

EXAMPLE 2

(3R,4R)-4-[3-Oxo-3-(3-fluoro-6-methoxyquinolin-4-yl)propyl]-1-[2-(2,5-difluorophenylsulfanyl)ethyl]piperidine-3-carboxylic acid A mixture of 0.1 g of methyl (3R,4R)-4-[3-oxo-3-(3-fluoro-6-methoxyquinolin-4-yl)propyl]-1-[2-(2,5-difluorophenylsulfanyl)ethyl]piperidine-3-carboxylate in 2 cm³ of 5N hydrochloric acid is brought to a temperature in the region of 80° C. with stirring and under an inert atmosphere for 5 hours. After cooling to around 20° C., the reaction medium is neutralized with 1.8 cm³ of 5N sodium hydroxide until a pH of 6 is obtained, and is then extracted with 20 cm³ of dichloromethane. The organic phase is dried over magnesium sulfate, filtered, and then evaporated to dryness under reduced pressure (2 kPa) at a temperature in the region of 30° C. The residue obtained is purified by chromatography on a column of silica gel (particle size 70–200 µm; diameter 2 cm), eluting with a mixture of dichloromethane-methanol-aqueous ammonia (28%) (40/5/0.5 by volume) and collecting fractions of 10 cm³. The fractions containing the expected product are pooled and then evaporated according to the conditions described above. 0.072 g of (3R,4R)-4-[3-oxo-3-(3-fluoro-6-methoxyquinolin-4-yl)propyl]-1-[2-(2,5-difluorophenylsulfanyl)ethyl]piperidine-3-carboxylic acid, in the form of a beige-colored solid, is obtained.

¹H NMR spectrum (300 MHz, (CD₃)₂SO d6, δ in ppm): from 1.55 to 1.90 (mt: 5H); 2.29 (mt: 1H); 2.44 (broad d, J=12 Hz: 1H); 2.61 (mt: 1H); 2.68 (t, J=7 Hz: 2H); 2.79 (mt: 1H); 2.97 (mt: 1H); 3.12 (mt: 2H); 3.20 (broad t, J=6 Hz: 2H); 3.91 (s: 3H); from 7.00 to 7.15 (mt: 1H); 7.09 (d, J=3 Hz: 1H); from 7.20 to 7.40 (mt: 2H); 7.47 (dd, J=9 and 3 Hz: 1H); 8.05 (d, J=9 Hz: 1H); 8.89 (d, J=0.5 Hz: 1H); from 12.80 to 13.20 (broad unresolved peak: 1H).

Methyl (3R,4R)-4-[3-oxo-3-(3-fluoro-6-methoxyquinolin-4-yl)propyl]-1-[2-(2,5-difluorophenylsulfanyl)ethyl]-piperidine-3-carboxylate A mixture of 0.57 g of methyl (3R,4R)-4-[3-oxo-3-(3-fluoro-6-methoxyquinolin-4-yl)propyl]piperidine-3-carboxylate obtained as described in example 1, 0.462 g of 2-(2-bromoethylsulfanyl)-1,4-difluorobenzene, 0.253 g of potassium iodide and 1.05 g of potassium carbonate in 25 cm³ of acetonitrile is heated with stirring and under an inert atmosphere for 20 hours at a temperature in the region of 75° C. After cooling to a temperature in the region of 20° C., the reaction medium is filtered and the insoluble material is washed with 2 times 10 cm³ of acetonitrile. The filtrate is evaporated under reduced pressure (2 kPa) at a temperature in the region of 40° C. The evaporation residue is taken up with 50 cm³ of distilled water and 100 cm³ of ethyl acetate. The organic phase is washed with 3 times 30 cm³ of distilled water and 2 times 50 cm³ of a saturated aqueous sodium chloride solution, dried over magnesium sulfate and evaporated according to the conditions mentioned above. The oil obtained is purified by chromatography on a column of silica gel (particle size 70–200 µm; diameter 2.5 cm), eluting with a mixture of dichloromethane-methanol (9/10 by volume) and collecting fractions of 10 cm³. The fractions containing the expected product are pooled and then evaporated under reduced pressure (2 kPa) at a temperature in the region of 40° C. 0.4 g of methyl (3R,4R)-4-[3-oxo-3-(3-fluoro-6-methoxyquinolin-4-yl)propyl]-1-[2-(2,5-difluorophenylsulfanyl)ethyl]-piperidine-3-carboxylate, in the form of an orange-colored viscous oil, is obtained.

¹H NMR spectrum (300 MHz, (CD₃)₂SO d6, δ in ppm): 1.56 (mt: 1H); from 1.65 to 2.00 (mt: 4H); 2.24 (mt: 1H); 2.40 (broad d, J=12 Hz: 1H); from 2.50 to 2.70 (mt: 3H); 2.72 (mt: 1H); 2.85 (mt: 1H); 3.04 (mt: 2H); 3.12 (t, J=7 Hz: 2H); 3.57 (s: 3H); 3.90 (s: 3H); from 7.00 to 7.10 (mt: 1H); 7.09 (d, J=3 Hz: 1H); from 7.20 to 7.35 (mt: 2H); 7.48 (dd, J=9 and 3 Hz 1H); 8.05 (d, J=9 Hz: 1H); 8.89 (s: 1H).

EXAMPLE 3

(3RS,4RS)-4-[3-oxo-3-(3-fluoro-6-methoxyquinolin-4-yl)propyl]-1-[2-(2,5-difluorophenylsulfanyl)ethyl]piperidine-3-acetic acid A mixture of 0.3 g of methyl (3RS,4RS)-4-[3-oxo-3-(3-fluoro-6-methoxyquinolin-4-yl)propyl]-1-[2-(2,5-difluorophenylsulfanyl)ethyl]piperidine-3-acetate in 1.34 cm³ of a 1N aqueous sodium hydroxide solution and 5 cm³ of dioxane is brought to a temperature in the region of 60° C. with stirring and under an inert atmosphere for 1 hour. After cooling to around 20° C., the reaction medium is evaporated to dryness under reduced pressure (2 kPa) at a temperature in the region of 50° C. The evaporation residue obtained is taken up with 20 cm³ of water and 20 cm³ of diethyl ether, and the aqueous phase is separated after settling out and neutralized with 1.3 cm³ of 1N aqueous hydrochloric acid solution and is then extracted with 70 cm³ of ethyl acetate. The organic phase is dried over magnesium sulfate, filtered, and then evaporated according to the same conditions above. 0.23 g of (3RS,4RS)-4-[3-oxo-3-(3-fluoro-6-methoxyquinolin-4-yl)-propyl]-1-[2-(2,5-difluoro-phenylsulfanyl)ethyl]piperidine-3-acetic acid, in the form of a beige-colored solid, is obtained.

¹H NMR spectrum (300 MHz, (CD₃)₂SO d6, δ in ppm): 1.32 (very broad t, J=13.5 Hz: 1H); 1.49 (broad d: J=13.5 Hz: 1H); from 1.50 to 1.75 (mt: 3H); from 1.90 to 2.20 (mt: 3H); 2.20 (d mt, J=16.5 Hz: 1H); 2.47 (dd, J=16.5 and 9 Hz: 1H); from 2.50 to 2.70 (mt: 2H); 2.78 (mt: 2H); 3.06 (t, J=7.5 Hz: 2H); 3.12 (t, J=7 Hz: 2H); 3.90 (s: 3H); from 7.00 to 7.15 (mt: 1H); 7.10 (d, J=3 Hz: 1H); from 7.20 to 7.35 (mt: 2H); 7.47 (dd, J=9 and 3 Hz: 1H); 8.04 (d, J=9 Hz: 1H); 8.88 (s: 1H).

Methyl (3RS,4RS)-4-[3-oxo-3-(3-fluoro-6-methoxyquinolin-4-yl)propyl]-1-[2-(2,5-difluorophenylsulfanyl)ethyl]-piperidine-3-acetate 1.88 cm³ of dimethyl sulfoxide in 6 cm³ of dichloromethane are poured, over 10 minutes, over a solution of 1.32 cm³ of oxalyl dichloride in 30 cm³ of dichloromethane cooled to −70° C., with stirring and under an inert atmosphere. After 10 minutes, a solution of 1.7 g of methyl (3RS,4RS)-4-[3-(R,S)-hydroxy-3-(3-fluoro-6-methoxyquinolin-4-yl)propyl]-1-[2-(2,5-difluorophenylsulfanyl)ethyl]piperidine-3-acetate in 15 cm³ of dichloromethane is poured in 10 minutes. After 15 minutes, 8.4 cm³ of triethylamine in 10 cm³ of dichloromethane are added dropwise over 15 minutes and the reaction medium is stirred for 45 minutes in the region of −70° C. and then for 20 hours in the region of 20° C. 50 cm³ of distilled water are poured over the reaction mass, and the organic phase is separated after settling out, and washed with 50 cm³ of a saturated aqueous sodium hydrogen carbonate solution, with 2 times 30 cm³ of distilled water and with 30 cm³ of saturated aqueous sodium chloride solution. The organic extract is dried over magnesium sulfate, filtered, and evaporated under reduced pressure (2 kPa) at a temperature in the region of 40° C. The residue obtained is purified by chromatography under an argon pressure of 50 kPa, on a column of silica gel (particle size 40–60 μm; diameter 3 cm), eluting with a mixture of cyclohexane-ethyl acetate (60/40 by volume) and collecting fractions of 10 cm³. The fractions containing the expected product are pooled and then evaporated according to the conditions described above. 1.37 g of methyl (3RS,4RS)-4-[3-oxo-3-(3-fluoro-6-methoxyquinolin-4-yl)propyl]-1-[2-(2,5-difluorophenylsulfanyl)ethyl]piperidine-3-acetate are obtained.

Infrared spectrum: (CCl₄) 2930; 1737; 1701; 1621; 1506; 1484; 1468; 1232; 1189; 1166; 1028; 905 and 834 cm⁻¹

Methyl (3RS,4RS)-4-[3-(R,S)hydroxy-3-(3-fluoro-6-methoxyquinolin-4-yl)propyl]-1-[2-(2,5-difluorophenyl-sulfanyl)ethyl]piperidine-3-acetate A mixture of 6.5 g of methyl (3RS,4RS)-4-[3-(R,S)-hydroxy-3-(3-fluoro-6-methoxyquinolin-4-yl)propyl]-piperidine-3-acetate dihydrochloride, 3.9 g of 2-(2-bromoethylsulfanyl)-1,4-difluorobenzene dissolved in 10 cm³ of dimethylformamide, 2.32 g of potassium iodide, 5.8 g of potassium carbonate and 3.93 cm³ of triethylamine in 200 cm³ of acetonitrile is heated with stirring and under an inert atmosphere for 22 hours at a temperature in the region of 70° C. After cooling to a temperature in the region of 20° C., the reaction medium is filtered and the insoluble material is washed with 2 times 30 cm³ of acetonitrile. The filtrate is evaporated under reduced pressure (2 kPa) at a temperature in the region of 40° C. The evaporation residue is taken up with 100 cm³ of distilled water and 150 cm³ of ethyl acetate. The organic phase is washed with 3 times 100 cm³ of distilled water and 2 times 100 cm³ of a saturated aqueous sodium chloride solution, dried over magnesium sulfate, and evaporated according to the conditions described above. The oil obtained is purified by chromatography under an argon pressure of 50 kPa, on a column of silica gel (particle size 40–60 μm; diameter 4 cm), eluting with a mixture of cyclohexane-ethyl acetate (50/50 by volume) and collecting fractions of 60 cm³. The fractions containing the expected product are pooled and then evaporated under reduced pressure (2 kPa) at a temperature in the region of 40° C. 1.7 g of methyl (3RS,4RS)-4-[3-(R,S)-hydroxy-3-(3-fluoro-6-methoxyquinolin-4-yl)propyl]-1-[2-(2,5-difluorophenylsulfanyl)ethyl]piperidine-3-acetate, in the form of an orange-colored viscous oil, are obtained.

¹H NMR spectrum (300 MHz, (CD₃)₂SO d6, δ in ppm). A mixture of two diastereoisomers in 50/50 proportions is observed: from 0.90 to 2.60 (mt: 14H); from 2.60 to 2.80 (mt: 2H); 3.08 (broad t, J=7 Hz: 2H); 3.47 and 3.55 (2 s: 3H in all); 3.89 (s: 3H); 5.33 (very broad t, J=7 Hz: 1H); 5.83 (broad s: 1H); 7.05 (mt: 1H); from 7.15 to 7.35 (mt: 2H); 7.38 (d mt, J=9 Hz: 1H); from 7.90 to 8.00 (mt: 2H); 8.68 (broad s 1H).

Methyl (3RS,4RS) and (3SR,4RS)-4-[3-(R,S)-hydroxy-3-(3-fluoro-6-methoxyquinolin-4-yl)propyl]piperidine-3-acetate dihydrochloride A solution of 940 mg of (3RS,4RS) and (3SR,4RS)-4-[3-(R,S)-hydroxy-3-(3-fluoro-6-methoxyquinolin-4-yl)propyl]-1-(tert-butyloxycarbonyl)piperidine-3-acetic acid in 20 cm³ of methanol is cooled to a temperature in the region of −25° C., with stirring and under an inert atmosphere. 0.43 cm³ of thionyl chloride is added to this solution over 5 minutes. The mixture is brought back to a temperature in the region of 20° C., while the stirring is continued for a further 1 hour 30 minutes. The reaction mixture is concentrated under reduced pressure (5 kPa) at a temperature in the region of 40° C. and 30 cm³ of methanol are then added. This series of operations is repeated 3 times. 920 mg of methyl (3RS,4RS) and (3SR,4RS)-4-[3-(R,S)-hydroxy-3-(3-fluoro-6-methoxyquinolin-4-yl)propyl]piperidine-3-acetate dihydrochloride, in the form of a yellow foam, are obtained.

Infrared spectrum (KBr): 3249; 1949; 2503; 2020; 1731; 1622; 1604; 1555; 1497; 1457; 1420; 1308; 1242; 1200; 1175; 1080; 1014; 872; 832 and 795 cm⁻¹

(3RS,4RS) and (3SR,4RS)-4-[3-(R,S)-hydroxy-3-(3-fluoro-6-methoxyquinolin-4-yl)propyl]-1-(tert-butyloxycarbonyl)piperidine-3-acetic acid A solution of 1.16 g of methyl (3RS,4RS) and (3SR,4RS)-4-[3-(3-fluoro-6-methoxyquinolin-4-yl)-3-propyl]-1-(tert-butyloxycarbonyl)piperidine-3-acetate, 100 cm³ of anhydrous dimethylsulfoxide and 25 cm³ of anhydrous tert-butanol is stirred under an inert atmosphere free of water at 20° C. This colorless solution is purged with pure oxygen until saturation of the reaction mixture is obtained. A solution containing 685 mg of potassium tert-butoxide in 8 cm³ of anhydrous tert-butanol is then added. Oxygen is again introduced by sparging for a further 3 hours 30 minutes with vigorous stirring. The yellow solution obtained is purged with nitrogen and then cooled to 0° C. 0.5 cm³ of pure acetic acid in 20 cm³ of water and then 200 cm³ of ether are subsequently added. The organic phase is separated after settling out, washed with 7 times 20 cm³ of water and with 3 times 20 cm³ of a saturated aqueous sodium chloride solution, dried over magnesium sulfate, filtered, and concentrated under reduced pressure (5 kPa) at a temperature in the region of 40° C. A gum is obtained which is taken up in 20 cm³ of ether. The mixture is again concentrated under the same conditions as above. 945 mg of (3RS,4RS) and (3SR,4RS)-4-[3-(R,S)-hydroxy-3-(3-fluoro-6-methoxyquinolin-4-yl)propyl]-1-(tert-butyloxycarbonyl)piperidine-3-acetic acid, in the form of a white foam, are obtained.

Infrared spectrum (KBr): 2973; 2932; 2864; 1693; 1668; 1623; 1510; 1468; 1429; 1366; 1232; 1166; 1030 and 831 cm⁻¹

Infrared spectrum (CH₂Cl₂): 3600; 2982; 2939; 2867; 1710; 1682; 1623; 1509; 1468; 1429; 1367; 1231; 1162; 1030; 909; 896 and 834 cm⁻¹

Methyl (3RS,4RS) and (3SR,4RS)-4-[3-(3-fluoro-6-methoxyquinolin-4-yl)-3-propyl]-1-(tert-butyloxycarbonyl)piperidine-3-acetate A solution of 1.85 g of methyl (3RS,4RS) and (3SR,4RS)-4-[3-(3-fluoro-6-methoxyquinolin-4-yl)propyl]-piperidine-3-acetate, 0.7 cm³ of triethylamine and 40 cm³ of dichloromethane is cooled to a temperature in the region of 0° C., with stirring and under an argon atmosphere. A solution of 1.16 g of di-tert-butyl dicarbonate dissolved in 40 cm³ of dichloromethane is added to this colorless solution over 20 minutes. The mixture is returned to a temperature in the region of 20° C., while the stirring is continued for a further 10 hours. 200 cm³ of water are then added to the reaction mixture. The organic phase is separated after settling out, washed with 100 cm³ of a saturated aqueous sodium chloride solution, dried over magnesium sulfate, filtered, and then concentrated under reduced pressure (5 kPa) at a temperature in the region of 40° C. An oil is obtained which is purified by chromatography, under a nitrogen pressure of 50 kPa, on a column of silica gel (particle size 20–45μ; diameter 2 cm; height 20 cm), eluting with a mixture of cyclohexane-ethyl acetate (70/30 by volume) and collecting fractions of 40 cm³. Fractions 8 to 12 are pooled, and then concentrated as above. 2.16 g of methyl (3RS,4RS) and (3SR,4RS)-4-[3-(3-fluoro-6-methoxyquinolin-4-yl)-3-propyl]-1-(tert-butyloxycarbonyl)piperidine-3-acetate, in the form of a colorless oil, are obtained.

Infrared spectrum ($CCl_4$) 3006; 1740; 1695; 1622; 1507; 1468; 1428; 1366; 1231; 1166; 1034; 909 and 832 $cm^{-1}$ Methyl (3RS,4RS) and (3SR,4RS)-4-[3-(3-fluoro-6-methoxyquinolin-4-yl)propyl]piperidine-3-acetate 2.65 g of methyl (4RS)-1-benzyloxycarbonyl-4-[3(3-fluoro-6-methoxyquinolin-4-yl)propyl]piperidine-3-ylideneacetate, the Z isomer, 45 cm³ of absolute ethanol and 265 mg of palladium on charcoal at 10% are introduced into an autoclave. The reaction mixture is stirred under 5 bar of hydrogen at 22° C. for 24 hours, and then filtered over supercel and rinsed with 5 times 20 cm³ of absolute ethanol. The pooled filtrates are concentrated under reduced pressure (5 kPa) at a temperature in the region of 40° C. 1.85 g of methyl (3RS,4RS) and (3SR,4RS)-4-[3-(3-fluoro-6-methoxyquinolin-4-yl)propyl]piperidine-3-acetate, in the form of a colorless oil, are obtained.

¹H NMR spectrum (300 MHz, $(CD_3)_2SO$ d6, δ in ppm). from 1.10 to 1.80 (mt: 7H); from 1.90 to 2.30 (mt: 2H); from 2.35 to 2.60 (mt: 3H); from 2.65 to 2.95 (mt: 2H); 3.06 (mt: 2H); 3.55 and 3.56 (2s: 3H in all); 3.95 and 3.96 (2s: 3H in all); from 7.30 to 7.45 (mt: 2H); 7.96 (d, J=9 Hz: 1H); 8.70 (broad s: 1H).

Methyl (4RS)-1-benzyloxycarbonyl-4-[3-(3-fluoro-6-methoxyquinolin-4-yl)propyl]piperidine-3-ylidene acetate, Z isomer.

A solution of 5.8 g of methyl (4RS)-4-allyl-1-benzyloxycarbonylpiperidin-3-ylidene acetate (Z isomer) in 15 cm³ of tetrahydrofuran is added slowly, at a temperature in the region of 0° C., with stirring and under an inert atmosphere, to 45 cm³ of a 0.5 M solution of 9-borabicyclo[3,3,1]nonane in tetrahydrofuran. The mixture is then brought back to a temperature in the region of 20° C., while the stirring is continued for a further 4 hours. 5.5 g of 4-iodo-3-fluoro-6-methoxyquinoline in solution in 100 cm³ of tetrahydrofuran are added, followed by 11.2 g of tripotassium phosphate, and, finally, 386 mg of palladiumdiphenylphosphinoferrocene chloride. The reaction mixture is heated for 2 hours at reflux and then stirred for 48 hours at ambient temperature. The suspension obtained is filtered. The filtrate is concentrated and then taken up in 200 cm³ of ethyl acetate. The solution obtained is washed with 2 times 200 cm³ of water then with 2 times 200 cm³ of a saturated aqueous sodium chloride solution, dried over magnesium sulfate, filtered, and then concentrated under reduced pressure (5 kPa) at a temperature in the region of 40° C. 15 g of an oil are obtained, which is purified by chromatography, under a nitrogen pressure of 50 kPa, on a column of silica gel (particle size 20–45μ; diameter 6 cm; height 38 cm), eluting with a mixture of cyclohexane-ethyl acetate (85/15 by volume, forming a gradient up to 70/30 by volume) and collecting fractions of 200 cm³. Fractions 31 to 34 are pooled and then concentrated. 4.7 g of methyl (4RS)-1-benzyloxycarbonyl-4-[3-(3-fluoro-6-methoxyquinolin-4-yl)propyl]piperidine-3-ylidene acetate (Z isomer), in the form of a colorless oil, are obtained.

Infrared spectrum ($CCl_4$): 3091; 3068; 3034; 1705; 1655; 1622; 1507; 1468; 1434; 1361; 1263; 1231; 1207; 1173; 1141; 1034; 909; 832 and 696 $cm^{-1}$ Methyl (4RS)-4-allyl-1-benzyloxycarbonylpiperidin-3-ylidene acetate, Z isomer.

A solution containing 16.3 g of (4RS)-4-allyl-1-benzyloxycarbonylpiperidin-3-one in 200 cm³ of toluene is stirred at reflux with methyl (triphenylphosphoranylidene) acetate, under an inert atmosphere, for 16 hours. After cooling to approximately 20° C., the reaction mixture is concentrated under reduced pressure (5 kPa) at a temperature in the region of 40° C., and the residue obtained, solubilized in 50 cm³ of dichloromethane under hot conditions, is purified by chromatography, under a nitrogen pressure of 50 kPa, on a column of silica gel (particle size 20–45μ; diameter 10 cm; height 45 cm), eluting with a mixture of cyclohexaneethyl acetate (80/20 by volume) and collecting fractions of 250 cm³. Fractions 13 to 15 are pooled and then concentrated as above. 5.8 g of methyl (4RS)-4-allyl-1-benzyloxycarbonylpiperidin-3-ylidene acetate (Z isomer), in the form of a colorless oil, are obtained.

Infrared spectrum ($CCl_4$): 3068; 3034; 2949; 2853; 1722; 1705; 1655; 1643; 1434; 1260; 1200; 1174; 1144; 993; 918 and 696 $cm^{-1}$ The (4RS)-4-allyl-1-benzyloxycarbonylpiperidin-3-one may be prepared according to Y.Takeuchi et al., described in Synthesis 1999, 10, 1814.

EXAMPLE 4

(3R,4R)-4-[3-Oxo-3-(6-methoxyquinolin-4-yl)propyl]-1-[2-(2-thienylsulfanyl)ethyl]piperidine-3-carboxylic acid A mixture of 0.43 g of methyl (3R,4R)-4-[3-oxo-3-(6-methoxyquinolin-4-yl)propyl]-1-[2-(2-thienylsulfanyl)-ethyl]piperidine-3-carboxylate in 5 cm³ of 5N hydrochloric acid is brought to a temperature in the region of 80° C. with stirring and under an inert atmosphere for 5 hours. After cooling to around 20° C., the reaction medium is neutralized with 4.7 cm³ of 5N sodium hydroxide until a pH of 6 is obtained, and is then extracted with 30 cm³ of dichloromethane. The organic phase is dried over magnesium sulfate, filtered, and then evaporated to dryness under reduced pressure (2 kPa) at a temperature in the region of 30° C. The residue obtained is purified by chromatography on a column of silica gel (particle size 70–200 μm; diameter 2 cm), eluting with a mixture of chloroformmethanol-aqueous ammonia (28%) (12/3/0.5 by volume) and collecting fractions of 10 cm³. The fractions containing the expected product are pooled and then evaporated according to the conditions described above. 0.4 g of (3R,4R)-4-[3-oxo-3-(6-methoxyquinolin-4-yl)propyl]-1-[2-(2-thienylsulfanyl)ethyl]piperidine-3-carboxylic acid, in the form of a yellow-colored oil, is obtained.

¹H NMR spectrum (300 MHz, (CD₃)₂SO d6, δ in ppm): from 1.55 to 1.85 (mt: 5H); 2.35 (mt: 1H); from 2.40 to 2.50 (mt: 1H); from 2.60 to 2.75 (mt: 3H); 2.84 (mt: 1H); from 2.90 to 3.10 (mt: 3H); 3.19 (mt: 2H); 3.89 (s: 3H); 7.06 (dd, J=6 and 3.5 Hz: 1H); 7.22 (broad d, J=3.5 Hz: 1H); 7.48 (dd, J=9 and 3 Hz: 1H); 7.62 (dd, J=6 and 1 Hz: 1H); 7.73 (d, J=3 Hz: 1H); 7.91 (d, J=5 Hz: 1H); 8.02 (d, J=9 Hz: 1H); 8.88 (d, J=5 Hz: 1H).

Methyl (3R,4R)-4-[3-oxo-3-(6-methoxyquinolin-4-yl)propyl]-1-[2-(2-thienylsulfanyl)ethyl]piperidine-3-carboxylate A mixture of 0.95 g of methyl (3R,4R)-4-[3-oxo-3-(6-methoxyquinolin-4-yl)propyl]piperidine-3-carboxylate, 0.72 g of 2-(2-bromoethylsulfanyl)-2-thiophene, 0.44 g of potassium iodide and 1.9 g of potassium carbonate in 40 cm³ of acetonitrile is heated with stirring and under an inert atmosphere for 17 hours at a temperature in the region of 70° C. After cooling to a temperature in the region of 20° C., the reaction medium is filtered and the insoluble material is washed with 2 times 15 cm³ of acetonitrile. The filtrate is evaporated under reduced pressure (2 kPa) at a temperature in the region of 40° C. The evaporation residue is taken up with 50 cm³ of distilled water and 100 cm³ of ethyl acetate. The organic phase is washed with 3 times 30 cm³ of distilled water and 2 times 50 cm³ of a saturated aqueous sodium chloride solution, dried over magnesium sulfate and evaporated according to the conditions described above. The oil obtained is purified by chromatography on a column of silica gel (particle size 70–200 μm; diameter 2.5 cm), eluting with a mixture of ethyl acetate-petroleum ether (80/20 by volume) and collecting fractions of 10 cm³. The fractions containing the expected product are pooled and then evaporated under reduced pressure (2 kPa) at a temperature in the region of 40° C. 0.43 g of methyl (3R,4R)-4-[3-oxo-3-(6-methoxyquinolin-4-yl)propyl]-1-[2-(2-thienylsulfanyl)ethyl]piperidine-3-carboxylate, in the form of a brown-colored viscous oil, is obtained.

¹H NMR spectrum (300 MHz, (CD₃)₂SO d6, δ in ppm): 1.56 (mt: 1H); from 1.60 to 1.95 (mt: 4H); 2.21 (mt: 1H); 2.36 (broad d, J=12 Hz: 1H); from 2.40 to 2.60 (mt: 3H); from 2.70 to 2.85 (mt: 2H); 2.91 (t, J=7 Hz: 2H); from 3.00 to 3.30 (mt: 2H); 3.57 (s: 3H); 3.89 (s: 3H); 7.05 (dd, J=6 and 3.5 Hz: 1H); 7.18 (dd, J=3.5 and 1 Hz: 1H); 7.49 (dd, J=9 and 3 Hz: 1H); 7.61 (dd, J=6 and 1 Hz: 1H); 7.73 (d, J=3 Hz: 1H); 7.92 (d, J=5 Hz: 1H); 8.03 (d, J=9 Hz: 1H); 8.90 (d, J=5 Hz: 1H).

The methyl (3R,4R)-4-[3-oxo-3-(6-methoxyquinolin-4-yl)propyl]piperidine-3-carboxylate may be obtained using the method described in patent application FR 99 11679.

EXAMPLE 5

(3R,4R)-4-[3-Oxo-3-(6-methoxyquinolin-4-yl)propyl]-1-[3-(2,3,5-trifluorophenyl)prop-2-ynyl]piperidine-3-carboxylic acid A solution of 1 g of methyl (3R,4R)-4-[3-oxo-3-(6-methoxyquinolin-4-yl)propyl]-1-[3-(2,3,5-trifluorophenyl)prop-2-ynyl]piperidine-3-carboxylate in 10 cm³ of a 5N aqueous hydrochloric acid solution is stirred for 4 hours at a temperature in the region of 80° C. After cooling to a temperature in the region of 20° C., 10 cm³ of water, then 10 cm³ of chloroform, and then 1.9 g of powdered sodium hydrogen carbonate are added. The mixture is extracted with 3 times 10 cm³ of chloroform. The organic phases are pooled, dried over sodium sulfate, filtered, and then concentrated under reduced pressure (5 kPa) at a temperature in the region of 40° C. The residue obtained is purified by chromatography under a nitrogen pressure of 50 kPa, on a column of silica gel (particle size 20–45μ; diameter 2.5 cm; 30 g), eluting with a mixture of dichloromethane-methanol (96/4 by volume) and collecting first a fraction of 150 cm³, and then fractions of 10 cm³. Fractions 5 to 22 are pooled, and then concentrated as above. 0.583 g of (3R,4R)-4-[3-oxo-3-(6-methoxyquinolin-4-yl)propyl]-1-[3-(2,3,5-trifluorophenyl)prop-2-ynyl]piperidine-3-carboxylic acid, in the form of a green-colored solid which melts at around 70° C., is obtained.

¹H NMR spectrum (300 MHz, (CD₃)₂SO d6, δ in ppm): from 1.60 to 1.95 (mt: 5H); 2.44 (mt: 1H); 2.58 (broad d, J=11 Hz: 1H); 2.73 (mt: 2H); 2.92 (mt: 1H); 3.19 (mt: 2H); 3.67 (s: 2H); 3.88 (s: 3H); 7.32 (mt: 1H); 7.48 (dd, J=9 and 2.5 Hz: 1H); 7.63 (mt: 1H); 7.72 (d, J=2.5 Hz: 1H); 7.92 (d, J=4.5 Hz: 1H); 8.02 (d, J=9 Hz: 1H); 8.89 (d, J=4.5 Hz: 1H); from 12.30 to 12.80 (broad unresolved peak: 1H). Optical rotation: $\alpha_D^{20}$=+27.9° +/−0.8, in 0.5% methanol.

Methyl (3R,4R)-4-[3-oxo-3-(6-methoxyquinolin-4-yl)propyl]-1-[3-(2,3,5-trifluorophenyl)prop-2-ynyl]piperidine-3-carboxylate A mixture of 17.28 g of methyl (3R,4R)-4-[3-oxo-3-(6-methoxyquinolin-4-yl)propyl]-1-(prop-2-ynyl)-piperidine-3-carboxylate in 173 cm³ of triethylamine is stirred for 5 minutes under an inert atmosphere at a temperature in the region of 20° C. 4.05 g of tetrakis(triphenylphosphine)palladium, 0.834 g of cuprous iodide and 7.9 g of 1-bromo-2,3,5-trifluorobenzene are added. The mixture is stirred for 2 hours at a temperature in the region of 80° C. After cooling to approximately 20° C., 150 cm³ of ethyl acetate and 150 cm³ of water are added to the reaction mixture, which is then separated after settling out. The aqueous phase is extracted with 3 times 150 cm³ of ethyl acetate. The organic phases are pooled, washed with 5 times 150 cm³ of water, dried over sodium sulfate, filtered, and concentrated under reduced pressure (5 kPa) at a temperature in the region of 40° C. The residue obtained is purified by chromatography under a nitrogen pressure of 50 kPa, on a column of silica gel (particle size 20–45μ; diameter 7 cm; 600 g), eluting with pure ethyl acetate and collecting first a fraction of 2.5 l, and then fractions of 250 cm³. Fractions 2 to 29 are pooled and then concentrated as above. 18.4 g of methyl (3R,4R)-4-[3-oxo-3-(6-methoxyquinolin-4-yl)propyl]-1-[3-(2,3,5-trifluorophenyl)prop-2-ynyl]-piperidine-3-carboxylate, in the form of a yellow oil, are obtained.

¹H NMR spectrum (400 MHz, (CD₃)₂SO d6, δ in ppm): from 1.55 to 1.95 (mt: 5H); 2.39 (mt: 1H); 2.58 (broad d, J=10 Hz: 1H); 2.68 (mt: 1H); 2.82 (mt: 1H); 2.91 (mt: 1H); 3.09 (mt: 1H); 3.23 (mt: 1H); 3.58 (s: 2H); 3.88 (s: 3H); 7.31 (mt: 1H); 7.49 (dd, J=9 and 2.5 Hz: 1H); from 7.55 to 7.65 (mt: 1H); 7.73 (d, J=2.5 Hz: H); 7.92 (d, J=4.5 Hz: 1H); 8.02 (d, J=9 Hz: 1H); 8.89 (d, J=4.5 Hz: 1H).

What is claimed is:

1. A compound of the formula (I):

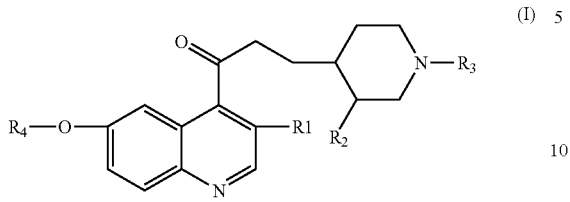

wherein:
- $R_1$ is hydrogen or fluorine;
- $R_2$ is carboxyl, carboxymethyl or hydroxymethyl;
- $R_3$ is $C_{1-6}$alkyl substituted with phenylthio, $C_{3-7}$ acycloalkylthio or 5- to 6-membered heteroarylthio; or propargyl substituted with phenyl, $C_{3-7}$cycloalkyl or 5- to 6-membered heteroaryl;
- wherein said heteroaryl is having 1 to 4 heteroatoms chosen from nitrogen, oxygen and sulfur; and
- wherein said phenyl or said heteroaryl is optionally substituted with one or more substituents selected from the group consisting of halogen, hydroxyl, alkyl, alkyloxy, trifluoromethyl, trifluoromethoxy, carboxyl, alkyloxycarbonyl, cyano and amino; and
- wherein said cycloalkyl is optionally substituted with one or more substituents chosen from halogen and trifluoromethyl; and
- $R_4$ is $C_{1-6}$alkyl, $C_{2-6}$alkenyl-$CH_2$— or $C_{2-6}$alkynyl-$CH_2$—, $C_{3-8}$cycloalkyl or $C_{3-8}$cycloalkylalkyl; or an isomer, an enantiomer, a diastereoisomer or a mixture thereof, or a pharmaceutically acceptable salt thereof.

2. The compound as set forth in claim 1, wherein $R_4$ is $C_{1-6}$alkyl.

3. The compound as set forth in claim 1, wherein $R_2$ is carboxyl.

4. The compound as set forth in claim 1, wherein $R_3$ is $C_{1-6}$alkyl substituted with an optionally substituted phenylthio, cycloalkylthio or heteroarylthio.

5. The compound as set forth in claim 4, wherein $R_3$ is ethyl substituted with thienylthio, phenylthio substituted with halogen or cyclohexylthio or cyclopentylthio.

6. The compound as set forth in claim 1, which is selected from the group consisting of:
- 1-(2-cyclohexylsulfanylethyl)-4-[3-(3-fluoro-6-methoxyquinolin-4-yl)-3-oxopropyl]piperidine-3-carboxylic acid,
- 4-[3-(3-fluoro-6-methoxyquinolin-4-yl)-3-oxo-propyl]-1-[3-(2,3,5-trifluorophenyl)prop-2-ynyl]piperidine-3-carboxylic acid,
- 4-[3-oxo-3-(3-fluoro-6-methoxyquinolin-4-yl)propyl]-1-[2-(2,5-difluorophenylsulfanyl)ethyl]piperidine-3-carboxylic acid,
- 4-[3-oxo-3-(3-fluoro-6-methoxyquinolin-4-yl)propyl]-1-[2-(2,5-difluorophenylsulfanyl)ethyl]piperidine-3-acetic acid,
- 4-[3-oxo-3-(6-methoxyquinolin-4-yl)propyl]-1-[2-(2-thienylsulfanyl)ethyl]piperidine-3-carboxylic acid, and
- 4-[3-oxo-3-(6-methoxyquinolin-4-yl)propyl]-1-[3-(2,3,5-trifluorophenyl)prop-2-ynyl]piperidine-3-carboxylic acid, or an isomer, an enantiomer, a diastereoisomer or a mixture thereof, or a pharmaceutically acceptable salt thereof.

7. A process for preparing a compound of formula (I) as set forth in claim 1, comprising condensing $R_3$—X with a compound of formula (II) or a corresponding ketone-protected compound of formula (II):

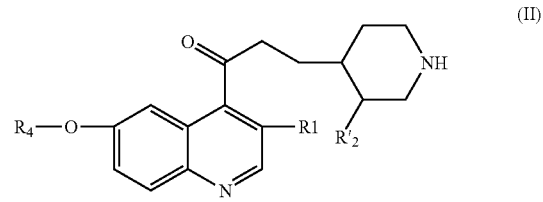

wherein $R_1$, $R_3$ and $R_4$ are as defined in claim 1; and
- $R_2'$ is protected carboxyl or carboxymethyl;
- X is halogen, methylsulfonyloxy, trifluoromethylsulfonyloxy or p-toluenesulfonyloxy; to obtain a compound of formula (III):

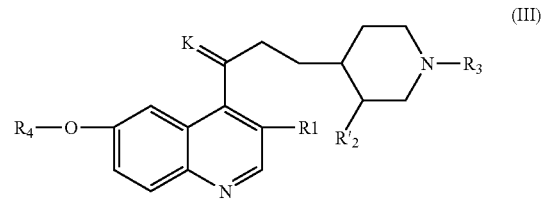

wherein $R_1$, $R'_2$, $R_3$ and $R_4$ are as defined above; and
- K is oxygen or a ketone-protecting group; and
- deprotecting the compound of formula (III) to form the compound of formula (I) wherein $R_2$ is carboxyl or carboxymethyl; and optionally
- reducing the carboxyl compound of formula (I) thus obtained or reducing directly the protected carboxyl compound of formula (III) to obtain a compound of formula (I) wherein $R_2$ is hydroxymethyl; and, optionally,
- converting said hydroxymethyl compound of formula (I) to a carboxymethyl compound of formula (I); and optionally
- separating the isomers, and removing the acid-protecting group, and the ketone-protecting group; and optionally converting said compound to a suitable salt.

8. A process for preparing a compound of formula (I) as set forth in claim 1 comprising condensing $R_3$—X with a compound of formula (II'):

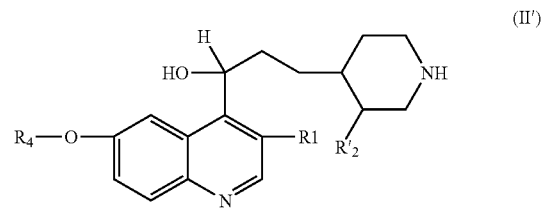

to obtain a compound of formula (III'):

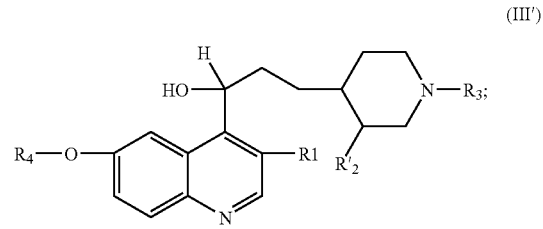

oxidizing the alcohol group in the alpha position of the quinoline to a ketone to obtain a compound formula (III):

(III)

wherein $R_1$, $R_3$ and $R_4$ are as defined in claim 1 and $R'_2$ is a protected carboxyl or carboxymethyl; and X is halogen, methylsulfonyloxy, trifluoromethylsulfonyloxy or p-toluenesulfonyloxy; and K is oxygen;

deprotecting the compound of formula (III) to form compound of formula (I) wherein $R_2$ is carboxyl or carboxymethyl; and optionally reducing the carboxyl compound of formula (I) thus obtained or reducing directly the protected carboxyl compound of formula (III) to obtain a compound of formula (I) wherein $R_2$ is hydroxymethyl; and, optionally, converting said hydroxymethyl compound of formula (I) to a carboxymethyl compound of formula (I); and optionally separating the isomers, and removing the acid-protecting group, and the ketone-protecting group; and optionally converting said compound to a suitable salt.

9. The process as set forth in claim 7, wherein the compound of formula (II) in which $R_1$ is fluorine is prepared by the reaction of a compound of formula (VI):

(VI)

with a compound of formula (VII):

(VII)

wherein $R_4$ is as defined in claim 7;

Rz is an amine-protecting group; and

Ra is an alkyl group;

to obtain a compound of formula (V):

(V)

oxidizing compound of formula (V) to obtain the corresponding compound of formula (I) in which $R_2$ is carboxyl; and optionally protecting the carboxyl and the ketone groups; and reducing the carboxyl to hydroxymethyl, and converting said hydroxymethyl to carboxymethyl; and deprotecting the ketone and the amine groups to obtain the compound of formula (II) in which $R_1$ is fluorine.

10. The process as set forth in claim 7 wherein the compound formed is selected from the group consisting of:

1-(2-cyclohexylsulfanylethyl)-4-[3-(3-fluoro-6-methoxyquinolin-4-yl)-3-oxopropyl]piperidine-3-carboxylic acid, 4-[3-(3-fluoro-6-methoxyquinolin-4-yl)-3-oxo-propyl]-1-[3-(2,3,5-trifluorophenyl)prop-2-ynyl]piperidine-3-carboxylic acid, 4-[3-oxo-3-(3-fluoro-6-methoxyquinolin-4-yl)propyl]-1-[2-(2,5-difluorophenylsulfanyl)ethyl]piperidine-3-carboxylic acid, 4-[3-oxo-3-(3-fluoro-6-methoxyquinolin-4-yl)propyl]-1-[2-(2,5-difluorophenyl-sulfanyl)ethyl]piperidin-e-3-acetic acid, 4-[3-oxo-3-(6-methoxyquinolin-4-yl)propyl]-1-[2-(2-thienylsulfanyl)ethyl]piperidine-3-carboxylic acid, and 4-[3-oxo-3-(6-methoxyquinolin-4-yl)propyl]-1-[3-(2,3,5-trifluorophenyl)prop-2-ynyl]piperidine-3-carboxylic acid, or an isomer, an enantiomer, a diastereoisomer or a mixture thereof, or a pharmaceutically acceptable salt thereof.

11. A pharmaceutical composition comprising therapeutically effective a mount of a compound of formula (I) as set forth in claim 1 or a pharmaceutically acceptable salt thereof, in combination with a pharmaceutically acceptable carrier.

12. A compound of formula (II):

(II)

wherein $R'_2$ is protected carboxyl or carboxymethyl;

$R_4$ is $C_{1-6}$alkyl, $C_{2-6}$alkenyl-$CH_2$— or $C_{2-6}$alkynyl-$CH_2$—, $C_{3-8}$cycloalkyl or $C_{3-8}$cycloalkylalkyl; and K is oxygen or a ketone-protecting group.

13. The compound as set forth in claim 12 wherein K is oxygen.

14. The compound as set forth in claim 12 wherein K is ketone-protecting group.

15. A compound of formula (A):

(A)

wherein $R_1$, $R_3$ and $R_4$ are as defined in claim 1, $R'_2$ is protected carboxyl or carboxymethyl and K is a ketone-protecting group.

16. A compound of formula (B):

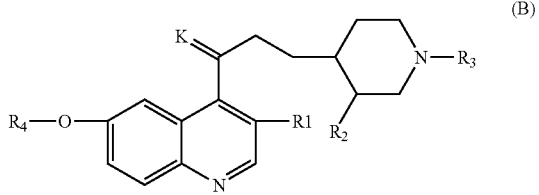

wherein $R_1$, $R_2$, $R_3$ and $R_4$ are as defined in claim 1 and K represents a ketone-protecting group.

17. A compound of formula (VIII):

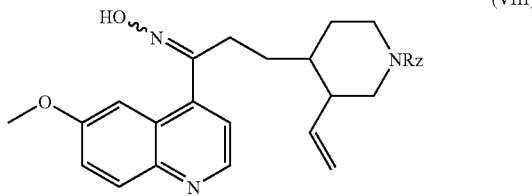

wherein Rz is an amine-protecting group.

18. A method of treatment of a bacterial infection in a patient comprising administering to said patient a therapeutically effective amount of a compound of formula (I) as set forth in claim 1 or a pharmaceutically acceptable salt thereof.

19. The method as set forth in claim 18 wherein said bacterial infection is caused by gram (+) bacteria.

20. The method as set forth in claim 18 wherein said bacterial infection is staphylococcic infection.

21. The method as set forth in claim 20 wherein said staphylococcic infection is selected from the group consisting of staphylococcal septicemias, malignant staphylococcic infections of the face or skin, pyoderma, septic or suppurant wounds, anthrax, phlegmons, erysipelas, acute primary or post-influenza staphylococcic infections, bronchopneumonias and pulmonary suppurations.

22. The method as set forth in claim 18 wherein said bacterial infection is colibacilloses and related infections, proteus infection, klebsiella infection, salmonella infection, and infection caused by gram (−) bacteria.

* * * * *